United States Patent
Nabutovsky et al.

(10) Patent No.: US 9,220,429 B2
(45) Date of Patent: Dec. 29, 2015

(54) SYSTEMS AND METHODS TO DETERMINE HR, RR AND CLASSIFY CARDIAC RHYTHMS BASED ON ATRIAL IEGM AND ATRIAL PRESSURE SIGNALS

(71) Applicant: Pacesetter, Inc., Sunnyvale, CA (US)

(72) Inventors: Yelena Nabutovsky, Sunnyvale, CA (US); Neal L. Eigler, Malibu, CA (US); Lok Man Chu, San Marino, CA (US); James S. Whiting, Los Angeles, CA (US); Jenner Joseph, Santa Clarita, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 235 days.

(21) Appl. No.: 13/838,732

(22) Filed: Mar. 15, 2013

(65) Prior Publication Data

US 2014/0275916 A1    Sep. 18, 2014

(51) Int. Cl.
| | |
|---|---|
| A61B 5/04 | (2006.01) |
| A61B 5/046 | (2006.01) |
| A61B 5/0464 | (2006.01) |
| A61B 5/0205 | (2006.01) |
| A61B 5/0215 | (2006.01) |
| A61B 5/00 | (2006.01) |
| A61B 5/042 | (2006.01) |
| A61B 5/0245 | (2006.01) |

(52) U.S. Cl.
CPC .......... *A61B 5/04014* (2013.01); *A61B 5/0006* (2013.01); *A61B 5/0205* (2013.01); *A61B 5/0215* (2013.01); *A61B 5/0422* (2013.01); *A61B 5/0464* (2013.01); *A61B 5/7253* (2013.01); *A61B 5/0245* (2013.01); *A61B 5/046* (2013.01); *A61B 5/742* (2013.01)

(58) Field of Classification Search
CPC .. A61B 5/04014; A61B 5/0205; A61B 5/046; A61B 5/0215; A61B 5/7253; A61B 5/742; A61B 5/0422; A61B 5/0006; A61B 5/0464; A61B 5/0245

See application file for complete search history.

(56) References Cited

U.S. PATENT DOCUMENTS

| | | | |
|---|---|---|---|
| 6,970,742 | B2 | 11/2005 | Mann et al. |
| 7,438,743 | B2 | 10/2008 | Strauss |
| 7,717,854 | B2 | 5/2010 | Mann et al. |
| 2004/0147969 | A1 | 7/2004 | Mann et al. |
| 2004/0167580 | A1 | 8/2004 | Mann et al. |
| 2006/0009810 | A1 | 1/2006 | Mann et al. |
| 2006/0079793 | A1 | 4/2006 | Mann et al. |
| 2007/0232936 | A1 | 10/2007 | Mann et al. |
| 2010/0057155 | A1 | 3/2010 | Farazi et al. |
| 2011/0125207 | A1* | 5/2011 | Nabutovsky et al. ............. 607/6 |
| 2014/0207005 | A1* | 7/2014 | Bukkapatnam et al. ...... 600/485 |

FOREIGN PATENT DOCUMENTS

WO    2005/000206    1/2005

* cited by examiner

*Primary Examiner* — Mark W Bockelman
(74) *Attorney, Agent, or Firm* — Theresa A. Raymer

(57) ABSTRACT

Systems, devices and methods described herein can be used to monitor and treat cardiovascular disease, and more specifically, can be used to determine heart rate (HR), determine respiration rate (RR) and classify cardiac rhythms based on atrial intracardiac electrogram (IEGM) and atrial pressure (AP) signals. The atrial IEGM and AP signals are subject to spectrum transforms to obtain an atrial IEGM frequency spectrum and an AP frequency spectrum. Based on peaks in the atrial IEGM and AP frequency spectrums measures of HR and RR are determined, and arrhythmias are detected and/or arrhythmia discrimination is performed.

7 Claims, 11 Drawing Sheets

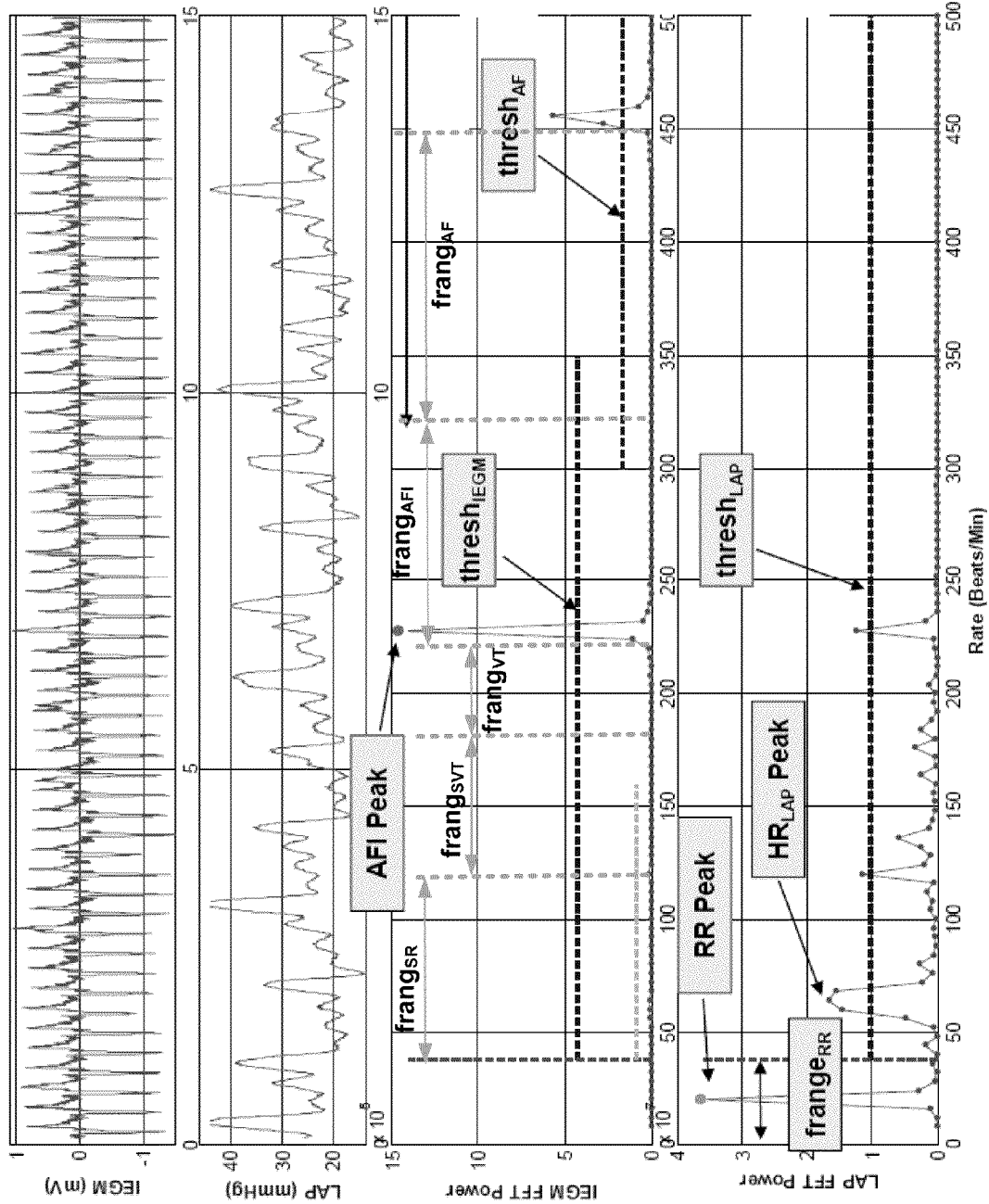

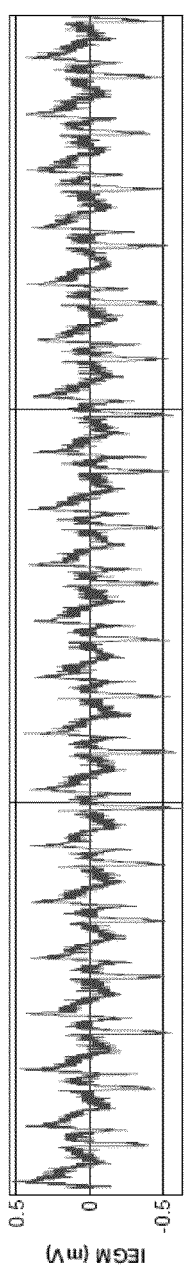
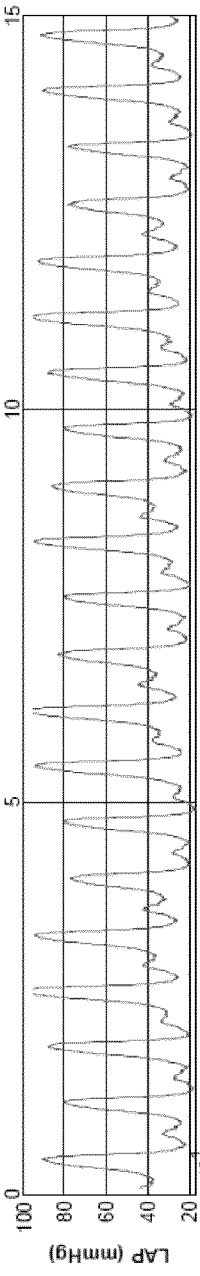
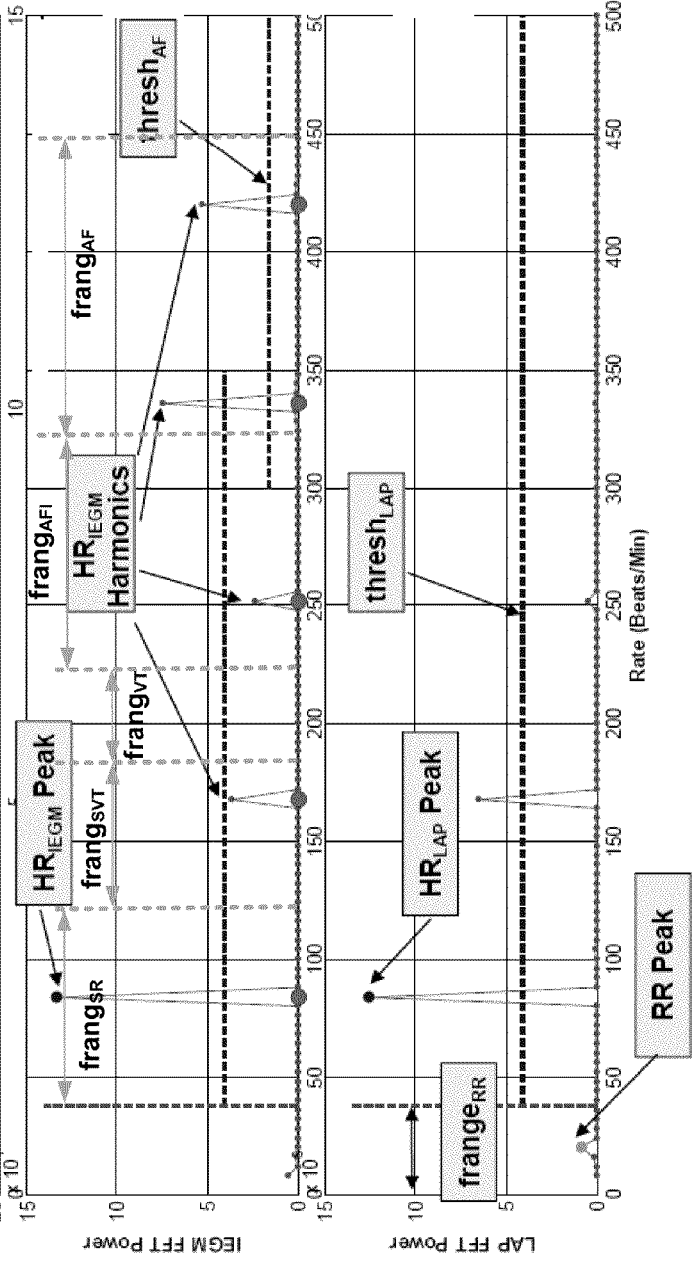
FIG. 5A
FIG. 5B
FIG. 5C
FIG. 5D

SYSTEMS AND METHODS TO DETERMINE HR, RR AND CLASSIFY CARDIAC RHYTHMS BASED ON ATRIAL IEGM AND ATRIAL PRESSURE SIGNALS

FIELD OF THE INVENTION

Embodiments of the present invention generally relate to systems, devices and methods that can be used to monitor and treat cardiovascular disease, and more specifically, can be used to determine heart rate (HR), determine respiration rate (RR) and classify cardiac rhythms based on atrial intracardiac electrogram (IEGM) and atrial pressure (AP) signals.

BACKGROUND

The optimum management of patients with chronic diseases requires that therapy be adjusted in response to changes in the patient's condition. Ideally, these changes are measured by daily patient self-monitoring prior to the development of symptoms. Self-monitoring and self-administration of therapy forms a closed therapeutic loop, creating a dynamic management system for maintaining homeostasis. Such a system can, in the short term, benefit day-to-day symptoms and quality-of-life, and in the long term, prevent progressive deterioration and complications.

There are tens of millions of people in the U.S. with risk factors for developing chronic cardiovascular diseases, including high blood pressure, diabetes, coronary artery disease, valvular heart disease, congenital heart disease, cardiomyopathy, and other disorders. Additional millions of patients have already suffered quantifiable structural heart damage but are presently asymptomatic. Still yet, there are millions of patients with symptoms relating to underlying heart damage defining a clinical condition known as congestive heart failure (CHF). Although survival rates have improved, the mortality associated with CHF remains worse than many common cancers. The number of CHF patients is expected to grow as the population ages and more people with damaged hearts are surviving.

CHF is a condition in which a patient's heart works less efficiently than it should, and a condition in which the heart fails to supply the body sufficiently with the oxygen-rich blood it requires, either during exercise or at rest. To compensate for this condition and to maintain blood flow (cardiac output), the body retains sodium and water such that there is a build-up of fluid hydrostatic pressure in the pulmonary blood vessels that drain the lungs. As this hydrostatic pressure overwhelms oncotic pressure and lymph flow, fluid drains from the pulmonary veins into the pulmonary interstitial spaces, and eventually into the alveolar air spaces. This complication of CHF is called pulmonary edema, which can cause shortness of breath, hypoxemia, acidosis, respiratory arrest, and death. Although CHF is a chronic condition, the disease often requires acute hospital care. Patients are commonly admitted for acute pulmonary congestion accompanied by serious or severe shortness of breath. Acute care for CHF accounts for the use of more hospital days than any other cardiac diagnosis, and consumes billions of dollars in the United States annually.

Not all CHF patients suffer debilitating symptoms immediately. Some may live actively for years. Yet, with few exceptions, the disease is relentlessly progressive. As CHF progresses, it tends to become increasingly difficult to manage. Even the compensatory responses it triggers in the body may themselves eventually complicate the clinical prognosis. For example, when the heart attempts to compensate for reduced cardiac output, ventricular muscle mass increases due to increased work that ventricles must perform with each heartbeat. This places a still higher demand on the heart's oxygen supply. If the oxygen supply falls short of the growing demand, as it often does, further injury to the heart may result. The additional muscle mass may also stiffen the heart walls, which further reduces cardiac output.

Current standard treatment for CHF is typically centered around medical treatment using ACE inhibitors, diuretics, and digitalis. It has also been demonstrated that aerobic exercise may improve exercise tolerance, improve quality of life, and decrease symptoms. Cardiac surgery has also been performed on a small percentage of patients with particular etiologies. Although advances in pharmacological therapy have significantly improved the survival rate and quality of life of patients, some CHF patients are refractory to drug therapy, have limited exercise tolerance, and a poor prognosis. In recent years, cardiac pacing, in particular Cardiac Resynchronization Therapy (CRT), has emerged as an effective treatment for many patients with drug-refractory CHF.

CHF patients require close medical management to reduce morbidity and mortality. Because the disease status evolves over time, frequent physician follow-up examinations are often necessary. At follow-up, the physician may make adjustments to the drug regimen in order to optimize therapy. This conventional approach of periodic follow-up may be less satisfactory for CHF, in which acute, life-threatening exacerbations can develop between physician follow-up examinations. It is well known among clinicians that if a developing exacerbation is recognized early, it can be more easily and inexpensively terminated, typically with a modest increase in oral diuretic. However, if it develops beyond the initial phase, an acute CHF exacerbation becomes difficult to control and terminate. Hospitalization in an intensive care unit is often required. It is during an acute exacerbation of CHF that many patients succumb to the disease. Early identification may also allow for pacing therapy from an implanted pulse generator. In view of the above, it would be beneficial if a patient's CHF condition could be chronically monitored.

In a normal heart, cells of the sinoatrial node (SA node) spontaneously depolarize and thereby initiate an action potential. This action potential propagates rapidly through the atria (which contract), slowly through the atrioventricular node (AV node), the atrioventricular bundle (AV bundle or His bundle) and then to the ventricles, resulting in a ventricular contraction. This sequence of events is known as sinus rhythm (SR). Thus, in a normal heart, ventricular rhythm relies on conduction of action potentials through the AV node and AV bundle.

Cardiac rhythms that do not follow the normal sequence of events described above and/or have rates that are outside a normal range are known as arrhythmias. Those that result in a heart rate slower than normal are known as bradyarrhythmias; those that result in a faster heart rate than normal are called tachyarrhythmias. Tachyarrhythmias are further classified as supraventricular tachyarrhythmias (SVTs) and ventricular tachyarrhythmias (VTs). SVTs are generally characterized by abnormal rhythms that may arise in the atria or the atrioventricular node (AV node). Additionally, there are various types of different SVTs and various types of VTs that can be characterized. The most common SVTs are typically atrial flutter (AFL) and atrial fibrillation (AF). In addition, many SVTs involve the AV node, for example, AV nodal reentrant tachycardia (AVNRT) where the reentrant loop or circuit includes the AV node. Another type of SVT is an AV reentrant tachycardia (AVRT), where an AV reentrant circuit typically involves the AV node and an aberrant conducting bundle known as an accessory pathway that connects a ventricle to an atrium.

Atrial flutter (AFL) can result when an early beat triggers a "circus circular current" that travels in regular cycles around the atrium, pushing the atrial rate up to approximately 221 bpm to approximately 320 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even HF as a result of the continuing increased stress on the heart muscle. In some individuals, the ventricular rate may also be slower if there is increased block of impulses in the AV node, or faster if there is little or no block.

If the cardiac impulse fails to follow a regular circuit in the atrium and divides along multiple pathways, a chaos of uncoordinated beats results, producing AF. AF commonly occurs when the atrium is enlarged (usually because of heart disease). In addition, it can occur in the absence of any apparent heart disease. In AF, the atrial rate can increase to more than 320 bpm and cause the atria to fail to pump blood effectively. Under such circumstances, the ventricular beat may also become haphazard, producing a rapid irregular pulse. Although AF may cause the heart to lose approximately 20 to 30 percent of its pumping effectiveness, the volume of blood pumped by the ventricles usually remains within the margin of safety, again because the atrioventricular node blocks out many of the chaotic beats. Hence, during AF, the ventricles may contract at a lesser rate than the atria, for example, of approximately 125 bpm to approximately 175 bpm.

Overall, SVTs are not typically immediately life threatening when compared to ventricular arrhythmias, examples of which are discussed below.

Ventricular arrhythmias, which originate in the ventricles, include ventricular tachycardia (VT) and ventricular fibrillation (VF). Ventricular arrhythmias are often associated with rapid and/or chaotic ventricular rhythms. For example, sustained VT can lead to VF. In sustained VT, consecutive impulses arise from the ventricles at a rate of about 121 to 180 bpm. Such activity may degenerate further into disorganized electrical activity known as ventricular fibrillation (VF). In VF, disorganized action potentials can cause the myocardium to quiver rather than contract. Such chaotic quivering can greatly reduce the heart's pumping ability. Indeed, approximately two-thirds of all deaths from arrhythmia are caused by VF. A variety of conditions such as, but not limited to, hypoxia, ischemia, pharmacologic therapy (e.g., sympathomimetics), and asynchronous pacing may promote onset of ventricular arrhythmia.

It has been common practice for an implantable cardioverter defibrillator (ICD) to monitor heart rate, or more commonly the ventricular rate, of a patient and classify the cardiac condition of the patient based on this heart rate. For example, a tachyarrhythmia may be defined as any rate in a range above a designated threshold. This range is then divided into ventricular tachycardia and ventricular fibrillation zones. The ventricular tachycardia zone may be further divided into slow ventricular tachycardia and fast ventricular tachycardia zones. However, some implanted devices may include only a single atrial lead which does not include any electrode implanted in a ventricle. Despite this, it would be useful if the ventricular heart rate could be monitored using such a device.

As described above, both SVTs and ventricular arrhythmias may lead to ventricular rates in excess of 100 bpm. In other words, ventricular rates of SVTs can overlap with rates of tachycardias of ventricular origin. These SVTs are often well tolerated and require no intervention. Further, physically active patients can have heart rates during exercise that overlap with their tachycardia rates. Accordingly, discrimination of VT from SVT, including increased heart rates due to exercise, may require more than just knowledge of a patient's ventricular rate. In other words, using heart rate as the sole criterion to classify the cardiac condition of a patient is often not sufficient.

In those patients who have an implantable device with only a single atrial lead and no electrode implanted in a ventricle, it would be useful to detect arrhythmias and/or perform arrhythmia discrimination, e.g., so that a physician could monitor the patient's cardiovascular condition, and if appropriate, recommend the implantation of an ICD or pacemaker. More generally, it would be useful if such a device could obtain useful information that is accessible to the patient and/or the patient's physician to enable the patient's cardiovascular condition to be appropriately monitored and treated.

SUMMARY

Certain embodiments of the present invention generally relate to systems, devices and methods that can be used to monitor and treat cardiovascular disease, and more specifically, can be used to determine heart rate (HR), determine respiration rate (RR) and classify cardiac rhythms based on atrial intracardiac electrogram (IEGM) and atrial pressure (AP) signals.

Certain embodiments of the present invention are directed to a system that includes an implantable device including an electrically conductive housing and a single implantable lead attached to the implantable device, and methods for use therewith. The system can also include a non-implantable device configured to communicate with the implantable device. The single implantable lead can include a pressure sensor configured to be implanted in a patient's left atrium. Additionally, the lead has one or more electrodes, which includes an electrode configured to be implanted in the patient's right atrium. Using at least one of the electrode(s), and optionally the electrically conductive housing, an atrial intracardiac electrogram (IEGM) signal is obtained. Additionally, the pressure sensor is used to obtain an atrial pressure (AP) signal indicative of pressure in an atrium, e.g., a left atrial pressure (LAP) signal indicative of pressure in the left atrium. Alternatively, the atrial pressure signal can be indicative of right atrial pressure (RAP). In certain embodiments, more than one lead can be attached to the implantable device.

The atrial IEGM signal is subject to a spectrum transform to obtain an atrial IEGM frequency spectrum, which can be an atrial IEGM frequency power spectrum, but is not limited thereto. Similarly, the AP signal is subject to a spectrum transform to obtain an AP frequency spectrum, which can be an AP frequency power spectrum, but is not limited thereto. A first measure of heart rate ($HR_{IEGM}$) is determined based on one or more peaks in the atrial IEGM frequency spectrum. Additionally, or alternatively, a second measure of heart rate ($HR_{AP}$) and/or a measure of respiratory rate ($RR_{AP}$) is/are determined based on one or more peaks in the AP frequency spectrum. In accordance with an embodiment, an estimate of the patient's actual heart rate is based on at least one of the first and second measures of heart rate, which is available for saving, uploading and/or displaying, along with the measure of respiratory rate ($RR_{AP}$).

In accordance with an embodiment, one or more peaks is/are identified in the atrial IEGM frequency spectrum that exceed an IEGM threshold (thresh$_{IEGM}$) and is/are within a sinus rhythm frequency range (frange$_{SR}$). The first measure of heart rate (HR$_{IEGM}$) is determined based on such identified peak(s).

Further, one or more peaks is/are identified in the AP frequency spectrum that is/are within a respiratory rate frequency range (frange$_{RR}$). A measure of respiratory rate (RR$_{AP}$) is determined based on such peak(s).

Additionally, one or more peaks is/are identified in the AP frequency spectrum that exceeds an AP threshold (thresh$_{AP}$) and is/are above a minimum heart rate or within a heart rate frequency range (frange$_{HR}$). The second measure of heart rate (HR$_{AP}$) is determined based on such peak(s). In certain embodiments, any peak that is determined to be a harmonic of the measure of respiratory rate (RR$_{AP}$), or is within a specified range of the measure of respiratory rate (RR$_{AP}$), is not used to determined the second measure of heart rate (HR$_{AP}$).

In accordance with specific embodiments, arrhythmias are detected and/or arrhythmia discrimination is performed based on one or more peaks in the atrial IEGM frequency spectrum and one or more peaks in the AP frequency spectrum. This can include identifying one or more peaks, if any, in the atrial IEGM frequency spectrum that is/are within an atrial fibrillation (AF) frequency range (frange$_{AF}$) and/or an atrial flutter (AFI) frequency range (frange$_{AFI}$). This can also include using the first measure of heart rate (HR$_{IEGM}$) to classify the patient's cardiac rhythm as one of ventricular tachycardia (VT), supraventricular tachycardia (SVT) and sinus rhythm (SR).

This summary is not intended to be a complete description of the invention. Other features, aspects, objects and advantages of the invention can be obtained from a review of the specification, the figures, and the claims.

BRIEF DESCRIPTION OF THE DRAWINGS

FIGS. 4(a)-4(d) illustrate an exemplary atrial IEGM signal, LAP signal, atrial IEGM frequency power spectrum, and LAP frequency power spectrum, which correspond to a heart rate of 64 beats per minute, a respiration rate of 20 breaths per minute, and which are used to detect atrial flutter.

FIGS. 5(a)-5(d) illustrate an exemplary atrial IEGM signal, LAP signal, atrial IEGM frequency power spectrum, and LAP frequency power spectrum, which correspond to a heart rate of 84 beats per minute, a respiration rate of 20 breaths per minute, and which are used to detect sinus rhythm.

DETAILED DESCRIPTION

Figure 1A:
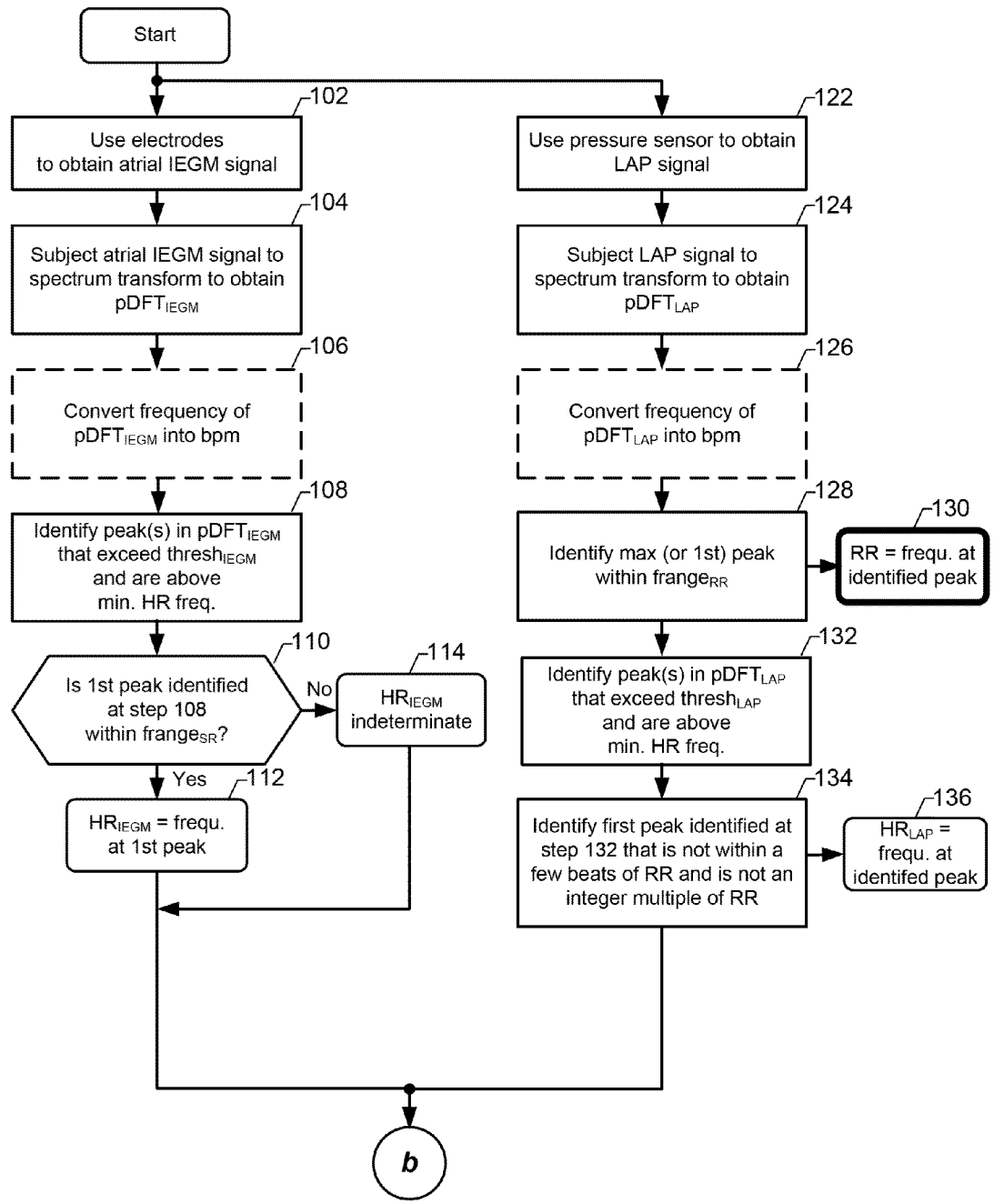
FIGS. 1(a)-1(b) illustrate a high level flow diagram that is used to summarize methods according to various embodiments of the present invention.

The following description is of the best modes presently contemplated for practicing various embodiments of the present invention. This description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. Also, the left-most digit(s) of a reference number identifies the drawing in which the reference number first appears.

Embodiments of the present invention generally relate to systems, devices and methods that can be used to monitor and treat cardiovascular disease, and more specifically, can be used to determine heart rate (HR), determine respiration rate (RR) and classify cardiac rhythms based on atrial intracardiac electrogram (IEGM) and atrial pressure (AP) signals. Heart rate (HR), as the term is used herein, refers to a patient's ventricular depolarization rate. By contrast, a patient's atrial depolarization rate will be referred to as the atrial rate. Both HR (i.e., ventricular depolarization rate) and atrial rate are typically expressed in beats per minute. RR is typically expressed in breaths per minute. Both beats per minute and breaths per minute can be represented by the same acronym "bpm", with the applicable unit determinable based on context.

Embodiments of the present invention are especially useful with an implantable device to which is attached only a single implantable atrial lead that includes as few as one electrode and an AP sensor, but are not limited thereto. Such an implantable device and lead (which can collectively be referred to as an implantable system) may be implanted, e.g., in a CHF patient.

Methods according to various embodiments of the present invention will first be described with reference to the high level flow diagrams of FIGS. 1A and 1B, which can be referred to collectively as FIG. 1, and the graphs of FIGS. 2A-2D, 3A-3D, 4A-4D and 5A-5D. FIGS. 2A-2D, 3A-3D, 4A-4D and 5A-5D include graphs illustrating atrial IEGM signals (see FIGS. 2A, 3A, 4A and 5A), LAP signals (see FIGS. 2B, 3B, 4B and 5B), atrial IEGM frequency power spectrums (see FIGS. 2C, 3C, 4C and 5C), and LAP frequency power spectrums (see FIGS. 2D, 3D, 4D and 5D).

Thereafter, devices and systems according to various embodiments of the present invention will be described with reference to FIGS. 6-10. For example, as will be described below with reference to FIGS. 6-10, embodiments of the present invention described with reference to FIGS. 1-5 can be used with a system that includes an implantable device including an electrically conductive housing, a single implantable lead attached to the implantable device, and a non-implantable device configured to communicate with the implantable device. As will be described below with reference to FIG. 6, the single implantable lead can include a pressure sensor configured to be implanted in a patient's left atrium, and one or more electrodes, one of which is configured to be implanted in the patient's right atrium.

Figures 2A, 2B, 2C, 2D:
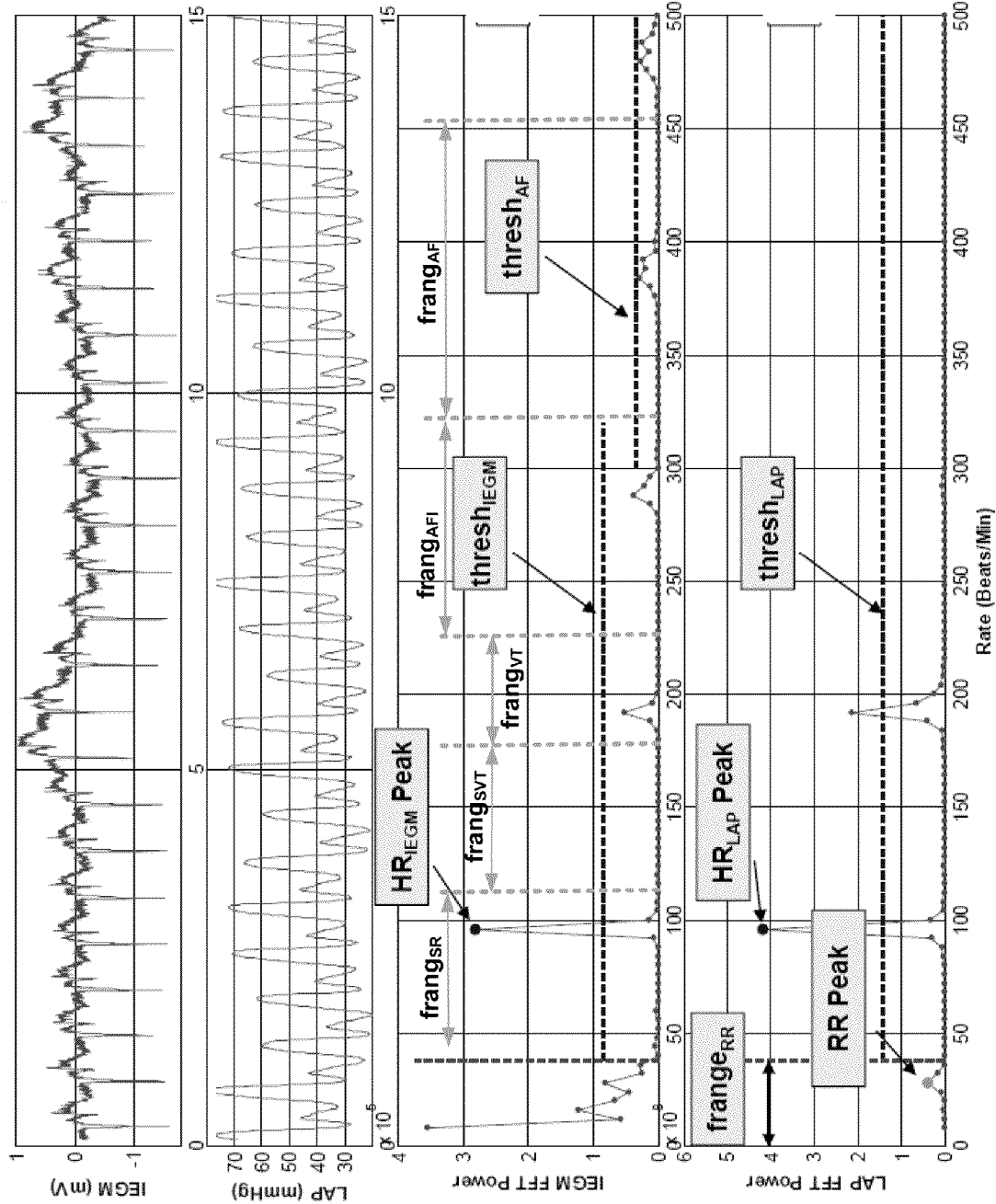
FIGS. 2(a)-2(d) illustrate an exemplary atrial IEGM signal, LAP signal, atrial IEGM frequency power spectrum, and LAP frequency power spectrum, which correspond to a heart rate of 96 beats per minute, a respiration rate of 28 breaths per minute, and which are used to detect sinus rhythm.

Referring now to FIG. 1A, at steps 102 and 122, an atrial IEGM signal and an LAP signal are obtained, e.g., using an implantable device to which is attached a single atrial lead. Exemplary atrial IEGM and LAP signals, which can be obtained at steps 102 and 122, are shown in FIGS. 2A and 2B, respectively. More specifically, at step 102, at least two electrodes are used to obtain the atrial IEGM, one of which is configured as an anode, and one of which is configured as a cathode. In accordance with an embodiment where the system includes only a single atrial lead, at least one of the electrodes used to obtain the atrial IEGM is an electrode of the single lead, wherein the electrode is implanted in the right atrium. For example, the atrial IEGM can be obtained using an electrode implanted within the right atrium configured as a cathode, and the electrically conductive housing (often referred to as the "can", "case" or "case electrode") of the implantable device (to which the lead is connected) configured as an anode. Where the single lead also includes a left atrial electrode (e.g., a left atrial tip or ring electrode), the atrial IEGM can alternatively be obtained between the electrode implanted within the right atrium and the electrode implanted within the left atrium. Other variations are also possible. For example, the atrial IEGM can be obtained using an electrode implanted in the right atrium, or in the inferior or superior vena cavea. Preferably, an electrode used to obtain the atrial IEGM is in contact with the atrial septum. The LAP signal is likely obtained using an LAP pressure sensor located at or near a distal end of the single lead, with the distal end of the lead being implanted in the left atrium. Additional details of a single lead including an LAP pressure sensor and one or more electrodes are described below with reference to FIGS. 6-10. Rather than obtaining an LAP signal at step 122 using a pressure sensor implanted in the left atrium, an alternative type of atrial pressure (AP) signal can be obtained. For example, it would also be possible that a right atrial pressure (RAP) signal be obtained and used in further steps described below. For the remaining discussion, unless stated otherwise, it will be assumed that the AP signal is an LAP signal. However, it is within the scope of an embodiment that an RAP signal be used in place of an LAP signal.

Note that in each of the above exemplary electrode configurations, there are no electrodes implanted in a ventricle, and thus, the atrial IEGM obtained using such configurations may not include clear-cut R-waves, making it more difficult to detect HR, which is typically detected based on R-R intervals between consecutive R-waves. Nevertheless, embodiments of the present invention enable a value for HR to be determined, as will be described below.

At step 104, the atrial IEGM signal is subject to a spectrum transform to obtain an atrial IEGM frequency spectrum, which is preferably an atrial IEGM frequency power spectrum. Similarly, at step 124, the LAP signal is subject to a spectrum transform to obtain an LAP frequency spectrum, which is preferably an atrial IEGM frequency power spectrum. In specific embodiments, steps 104 and 124 are accomplished by performing a discrete Fourier transform (DFT) on the atrial IEGM and LAP signals, in which case, the results of the transforms can be referred to, respectively, as $DFT_{IEGM}$ and $DFT_{LAP}$. In accordance with certain embodiments, the atrial IEGM and LAP signals are preconditioned before such a time domain to frequency domain conversion is performed. For example, the LAP signal can be high passed filtered (e.g., using a cutoff frequency of about 0.125 Hz) to remove the baseline, and the atrial IEGM signal can be low pass filtered (e.g., using a cutoff frequency of about 40 Hz) to remove noise. Such filtering can be performed in the analog domain. Alternatively, the filtering can be performed in the digital domain after the implantable device to which the lead is connected converts the atrial IEGM and LAP signals to digital signals using analog-to-digital converters (ADCs). After the filtering, the digital atrial IEGM and LAP signals can be padded with zeros (0s) in order to optimize the lengths of each signal for performing a Fourier transform. Thereafter, a DFT is performed on the atrial IEGM and on LAP signals to produce the $DFT_{IEGM}$ and the $DFT_{LAP}$, which are exemplary atrial IEGM and LAP frequency spectrums. A first point of the $DFT_{IEGM}$ and a first point of the $DFT_{LAP}$ is optionally removed. The power of the atrial IEGM and LAP frequency spectrums can then determined by squaring the absolute value of the first half of the points in the $DFT_{IEGM}$ and the $DFT_{LAP}$. The power of the atrial IEGM frequency spectrum can also be referred to as the atrial IEGM frequency power spectrum, or simply as $pDFT_{IEGM}$. The power of the LAP frequency spectrum can also be referred to as the LAP frequency power spectrum, or simply as $pDFT_{LAP}$. It is also within the scope of an embodiment of the present invention to not convert the atrial IEGM and LAP frequency spectrums to frequency power spectrums, so long as appropriate thresholds are used in the steps described below. For the following discussion, unless stated otherwise, it will be assumed that atrial IEGM and LAP frequency power spectrums are determined at steps 104 and 124. However, it is noted that the terms atrial IEGM and LAP frequency spectrums, as used hereafter, are meant to encompass both power and non-power frequency spectrums. Further, it is noted that alternative techniques than those described herein for determining the atrial IEGM and LAP frequency power spectrums (and non-power spectrums) are also possible, and within the scope of an embodiment of the present invention.

Preferably (but not necessarily), at steps 106 and 126, the frequencies of the atrial IEGM frequency power spectrum ($pDFT_{IEGM}$) and the LAP frequency power spectrum ($pDFT_{LAP}$) are converted to beats per minute (bpm). This can be accomplished by multiplying the frequencies by 60, which converts the frequencies from Hz to bpm. For the remainder of this description it will be assumed that steps 106 and 126 are performed. However, for those embodiments where steps 106 and 126 are not performed, the various thresholds and determinations described below will be in beats (or breaths) per second, instead of beats (or breaths) per minute. Exemplary atrial IEGM and LAP frequency power spectrum signals are shown in FIGS. 2(c) and 2(d), respectively.

At step 108, peaks in the atrial IEGM frequency power spectrum ($pDFT_{IEGM}$) that exceed a corresponding threshold ($thresh_{IEGM}$) and exceed a minimum HR frequency are identified. The minimum HR frequency can be, e.g., 39 bpm, but is not limited thereto. In specific embodiments, the minimum HR frequency can be defined based on the lower bound of a sinus rhythm (SR) frequency range ($frange_{RR}$), or based on the upper bound of an RR frequency range ($frange_{RR}$). In certain embodiments, the minimum HR frequency is determined experimentally to optimize sensitivity and/or specificity of HR and/or RR or some best case between the two. The $thresh_{IEGM}$ can be a programmed predetermined value. Alternatively, the $thresh_{IEGM}$ can be determined as part of (or prior to) step 108 based on the atrial IEGM frequency power spectrum obtained at step 104. For example, the $thresh_{IEGM}$ can be determined by computing a mean of the atrial IEGM frequency power spectrum and adding multiple (e.g., 2) standard deviations to the computed mean. Other techniques for determining the $thresh_{IEGM}$ are possible, and within the scope of an embodiment of the present invention. FIG. 2C includes an exemplary dashed horizontal line labeled $thresh_{IEGM}$ and a peak in the atrial IEGM frequency power spectrum (labeled $HR_{IEGM}$ Peak) that exceeds the $thresh_{IEGM}$.

If one or more peaks are identified at step 108, then there is a determination of whether the first identified peak (i.e., the peak corresponding to the lowest frequency that exceeds the minimum HR frequency) is within a sinus rhythm (SR) frequency range ($frange_{SR}$), as indicated at step 110. An exemplary $frange_{SR}$ is from 40 to 120 bpm, but is not limited thereto. If the first peak identified at step 108 is not within the $frange_{SR}$, or there is no peak that exceeds the $thresh_{IEGM}$, then it is concluded that HR can not be determined based on the atrial IEGM, and thus, an $HR_{IEGM}$ (i.e., an HR determination based on the atrial IEGM) is indeterminate, as specified at step 114. If the first peak identified at step 108 is within the $frange_{SR}$, then the $HR_{IEGM}$ is determined to be equal to, and is saved as, the frequency corresponding to the first peak identified at step 108, as indicated at step 112. For example, referring to FIG. 2C, the $HR_{IEGM}$ is shown as being approximately 96 bpm.

At step 128 the maximum peak in the LAP frequency power spectrum that is within the RR frequency range ($frange_{RR}$) is identified. Alternatively, at step 128 the first peak in the LAP frequency power spectrum that is within a $frange_{RR}$ is identified. An exemplary $frange_{RR}$ is from 9 to 39 bpm, but is not limited thereto. As indicated by step 130, the RR is determined to be equal to, and is saved as, a frequency corresponding to the peak identified at step 128. FIG. 2D illustrates a maximum peak (labeled RR Peak) in the LAP frequency power spectrum that is within the $frange_{RR}$. In FIG. 2D, the RR is shown as being approximately 28 bpm. The RR is useful for clinical analysis, e.g., to determine whether the patient is experiencing respiratory problems related to CHF, but is not limited thereto.

At step 132, peak(s) in the LAP frequency power spectrum ($pDFT_{LAP}$) that exceed a corresponding threshold ($thresh_{LAP}$) and exceed the minimum HR frequency are identified. As mentioned above, the minimum HR frequency can be, e.g., 39 bpm, but is not limited thereto. As also mentioned above, in specific embodiments, the minimum HR frequency can be defined based on the lower bound of the $frange_{SR}$, or based on the upper bound of the $frange_{RR}$. The $thresh_{LAP}$ can be a programmed predetermined value. Alternatively, the $thresh_{LAP}$ can be determined as part of (or prior to) step 132 based on the LAP frequency power spectrum obtained at step 124. For example, the $thresh_{LAP}$ can be determined by computing a mean of the LAP frequency power spectrum and adding multiple (e.g., 2) standard deviations to the computed mean. Other techniques for determining the $thresh_{LAP}$ are possible, and within the scope of an embodiment of the present invention. FIG. 2D includes an exemplary dashed horizontal line labeled $thresh_{LAP}$ and a peak (labeled $HR_{LAP}$ Peak) in the LAP frequency power spectrum that exceeds the $thresh_{LAP}$.

At step 134, there is an identification of the first peak identified at step 132 (i.e., the peak identified at step 132 corresponding to the lowest frequency) that is not within a relatively low predetermined number of beats (e.g., 3 beats) of the RR, and is not an integer multiple of the RR. As indicated at step 136, the frequency corresponding to the peak identified at step 134 is determined to be equal to, and is saved as, the $HR_{LAP}$, which is a value of HR determined based on the LAP signal. The reason to reject a peak within a few beats (e.g., within 3 beats) of the RR, is that such a peak is likely part of the RR peak. The reason to reject any peak that is an integer multiple (e.g., 2×, 3×, etc.) of the RR, is that such a peak is likely a harmonic of the RR. In exemplary FIG. 2D, the $HR_{LAP}$, which is determined based on the peak labeled $HR_{LAP}$ Peak, is approximately 96 bpm.

At this point, values for $HR_{LAP}$ and RR have been determined and saved, and a value for $HR_{IEGM}$ may also have been determined and saved (or there has been a determination that $HR_{IEGM}$ is indeterminate). In certain embodiments, the method stops here, or begins to repeat at this point. Such embodiments can be used to determine values for HR and RR, and to track changes in such values. In other embodiments, the method includes some or all of the additional steps described below with reference to FIG. 1B. As mentioned above, the AP signal obtained at step 122 need not be an LAP signal. Accordingly, the various references to LAP can more generally be references to AP. For examples, $pDFT_{LAP}$ can more generally be $pDFT_{AP}$, and $HR_{LAP}$ can more generally be $HR_{AP}$. However, for the remainder of this discussion, unless stated otherwise, it will be assumed that the AP signal is an LAP signal, and thus the terms $pDFT_{LAP}$ and $HR_{LAP}$ will typically be used for consistency.

In certain embodiments, the steps described with reference to FIG. 1A are performed within an implantable device, and the $HR_{LAP}$ and RR values, and potentially the $HR_{IEGM}$ value, are stored within the device (e.g., in memory and/or registers) and/or such values are wirelessly transmitted to an external (i.e., nonimplanted) device. In other embodiments, steps 102 and 122 are performed within an implantable device, and data corresponding to the signals obtained at step 102 and 122 are wirelessly transmitted to an external device that performs the remaining steps. For another example, the external device can save the signals obtained at step 102 and 122 so that they can be transferred (e.g., uploaded) to a further external device when a patient visits a physician or clinician, and the further device can perform the remaining steps. Such an external device can be, e.g., a patient advisory module (PAM), which can also be referred to as a personal advisory module. It is also possible that some of the steps are performed by one device (e.g., an implantable device), while other steps are performed by one or more other device (e.g., one or more non-implanted devices). Other variations are also possible, and within the scope of the present invention.

As will be appreciated from the following discussion of FIG. 1A, the values obtained by the steps of FIG. 1A along with additional analysis of the atrial IEGM and LAP frequency power spectrums ($pDFT_{IEGM}$ and $pDFT_{LAP}$) can be used to classify a cardiac rhythm. For example, arrhythmias can be detected and/or arrhythmia discrimination can be performed based on one or more peaks in the atrial IEGM power spectrum and one or more peaks in the LAP power spectrum.

Figure 1B:
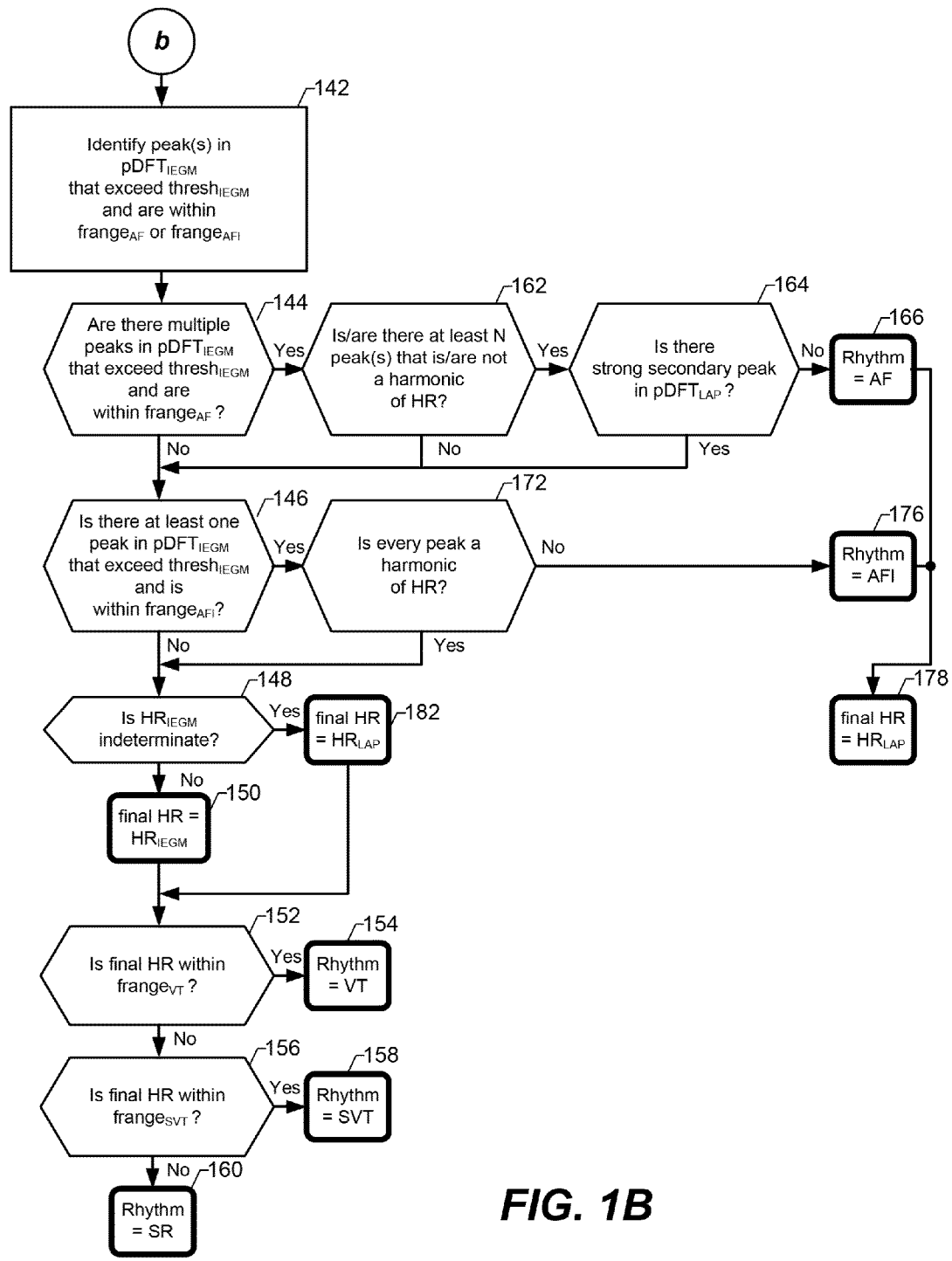

Referring now to FIG. 1B, at step 142, peak(s) in the atrial IEGM frequency power spectrum that is/are within an atrial fibrillation (AF) frequency range ($frange_{AF}$) or an atrial flutter (AFl) frequency range ($frange_{AFl}$), and exceed a corresponding threshold, is/are identified. The same threshold used at step 108 (i.e, $thresh_{IEGM}$) can be used at step 142. Alternatively, a lower threshold, referred to as the AF threshold ($thresh_{AF}$), can be used at step 142. The $thresh_{AF}$ can be a programmed predetermined value. Alternatively, the $thresh_{AF}$ can be determined as part of (or prior to) step 142 based on the atrial IEGM frequency power spectrum obtained at step 104. For example, the $thresh_{AF}$ can be determined by computing a mean of the atrial IEGM frequency power spectrum and making the $thresh_{AF}$ equal to the computed mean, or equal to the computed mean plus one standard deviation of the computed mean. For another example, the $thresh_{AF}$ can be equal to one-third (or some other fraction or percentage) of the $thresh_{IEGM}$. Other techniques for determining the $thresh_{AF}$ are possible, and within the scope of an embodiment of the present invention. FIG. 2C includes an exemplary dashed horizontal line labeled $thresh_{AF}$.

An exemplary frange$_{AFI}$ is from 221 to 320 bpm, and an exemplary frange$_{AF}$ is from 321 bpm-450 bpm. A supraventricular tachyarrhythmia (SVT) frequency range (frange$_{SVT}$) can also be defined, which is used to detect SVTs other than AF and AFI. An exemplary frange$_{SVT}$ is from 121 to 180 bpm. Additionally, a ventricular tachycardia (VT) frequency range (frange$_{VT}$) can also be defined, e.g., from 181 to 220 bpm. As mentioned above, an exemplary frange$_{SR}$ is from 40 to 120 bpm. Frequency ranges other than the exemplary ranges listed above can alternatively be used and be within the scope of an embodiment of the present invention.

At step 144 there is a determination of whether there are multiple peaks in the atrial IEGM frequency power spectrums (pDFT$_{IEGM}$) that exceed the thresh$_{IEGM}$ and are within the frange$_{AF}$. As mentioned above, an exemplary frange$_{AF}$ is from 321 bpm-450 bpm. If the answer to the determination at step 144 is yes, then at step 162 there is a determination of whether at least N of peaks in the atrial IEGM frequency power spectrums (pDFT$_{IEGM}$) (that exceed the thresh$_{IEGM}$ and are within the frange$_{AF}$) is/are not harmonic(s) of the HR. Here, N is a preprogrammed integer that can be equal to 1, 2, or more than 2. When N=1, the algorithm will provide more sensitivity, but less specificity. When N=2, the algorithm will provide less sensitivity, but more specificity. In accordance with an embodiment, the HR$_{IEGM}$ is used at step 162 (when determining whether a peak is a harmonic of the HR), assuming the HR$_{IEGM}$ was not considered indeterminate at steps 110 and 114. If the HR$_{IEGM}$ was considered indeterminate, then the HR$_{LAP}$ can be used at step 162, or alternatively, step 162 can be skipped.

Step 162 can be performed by determining whether each peak (in the atrial IEGM frequency power spectrums that exceeds the thresh$_{IEGM}$ and is within the frange$_{AF}$) is an integer multiple (e.g., 2×, 3×, etc.) of the HR. Step 162 can alternatively be performed by assuming that peaks separated from one another by a preprogrammed frequency (e.g., by at least 40 bpm) are harmonics of the HR. If the answer to the determination at step 162 is yes (i.e., if at least N of the peaks is/are not a harmonic of the HR), then at step 164 there is a determination of whether there is a strong secondary peak in the LAP frequency power spectrum (pDFT$_{LAP}$) at a frequency approximately twice the HR$_{LAP}$. In accordance with an embodiment, a strong secondary peak is defined as a peak having an amplitude that is within a predetermined percentage (e.g., 70%, or 75%) of the amplitude of the peak corresponding to the HR$_{LAP}$. If the answer to the determination at step 164 is no, then the cardiac rhythm is classified as AF, as shown at step 166, and an indication of the AF classification can be stored along with a time stamp and/or data corresponding to one or more of the signals and/or frequency power spectrums used for the AF classification. If the answer to the determination at step 164 is yes, then there will not be an AF classification, because such a large secondary peak would be indicative of prominent ventricular and atrial waves in the LAP signal (or more generally, the AP signal), which is indicative of a non-AF rhythm. The order of steps 162 and 164 can alternatively be reversed. It is also within the scope of an embodiment to remove or skip step 164 completely.

Alternatively, or additionally, one or more other steps can be performed to confirm or reject an AF classification. For example, an energy ratio can be determined based on the IEGM frequency power spectrum (pDFT$_{IEGM}$) and compared to a threshold. If the energy ratio exceeds the threshold, then an AF classification is confirmed. If the energy ratio does not exceed the threshold, then an AF classification is rejected. The energy ratio can be the ratio of the cumulative energy in the frange$_{AF}$ to the cumulative energy in the frange$_{SR}$. The energy ratio can alternatively be the ratio of the cumulative energy in the frange$_{AF}$ to the cumulative energy in the entire IEGM frequency power spectrum (pDFT$_{IEGM}$). In still another embodiment, the energy ratio can be the ratio of the cumulative energy in the potential AF peaks to the cumulative energy in the frange$_{SR}$.

If the answer to the determination at step 144 is no, the answer to the determination at step 162 is no, or the answer to the determination at step 164 is yes, then flow proceeds to step 146. At step 146 there is a determination of whether there is at least one peak in the atrial IEGM frequency power spectrum (pDFT$_{IEGM}$) that exceeds the thresh$_{IEGM}$ and is within the frange$_{AFI}$. As mentioned above, an exemplary frange$_{AFI}$ is from 221 to 320 bpm. If the answer to the determination at step 146 is yes, then at step 172 (which is similar to step 162 described above) there is a determination of whether each of the peaks identified at step 146 is a harmonic of the HR. In accordance with an embodiment, the HR$_{IEGM}$ is used at step 172 (when determining whether a peak is a harmonic of the HR), assuming the HR$_{IEGM}$ was not considered indeterminate at steps 110 and 114. If the HR$_{IEGM}$ was considered indeterminate, then the HR$_{LAP}$ can be used at step 172, or alternatively, step 172 can be skipped and flow can go directly to step 176. If the answer to the determination at step 172 is no (i.e., if at least one of the peaks is not an integer multiple of the HR), then the cardiac rhythm is classified as AFI, as shown at step 176, and an indication of the AFI classification can be stored along with a time stamp and/or data corresponding to one or more of the signals and/or frequency power spectrums used for the AFI classification. Additionally, as indicated at step 178, if there is an AF or AFI classification at one of steps 166 and 176, then the final HR is determined to be equal to, and is saved as, the HR$_{LAP}$. This is because the LAP signal is considered to provide a more accurate estimate of HR than the atrial IEGM signal during AF or AFI. The final HR can also be referred to as an estimate of the patient's actual HR.

If the cardiac rhythm is not classified as AF or AFI at one of steps 166 and 176, then there is a determination at step 148 of whether the HR$_{IEGM}$ was considered indeterminate. In accordance with an embodiment, if the answer to the determination at step 148 is no, then the final HR is determined to be equal to, and is saved as, the HR$_{IEGM}$, as indicated at step 150. If the answer to the determination at step 148 is yes, then the final HR is determined to be equal to, and is saved as, the HR$_{LAP}$, as indicated at step 182. More generally, in certain embodiments if there has been an AF or AFI classification, then the final HR is determined to be equal to, and is saved as, the HR$_{LAP}$. This is because the atrial IEGM is considered to provide a more accurate estimate of HR if the patient is not experiencing AF or AFI. Optionally, if there has been an AF classification, and there are more than a threshold number of peaks in the LAP frequency power spectrums (pDFT$_{LAP}$), then the final HR can be considered indeterminate. Optionally, if there has been an AFI classification, and there is more than a threshold amount of energy in the LAP frequency power spectrums (pDFT$_{LAP}$) within the frange$_{AFI}$, then the final HR can be considered indeterminate.

In certain embodiments, if the HR$_{LAP}$ and the HR$_{IEGM}$ are within a predetermined number of beats (e.g., 3 beats) of one another, either of the two, or the average of the two can be identified as, and saved as, the final HR. In certain embodiments, if the HR$_{LAP}$ and the HR$_{IEGM}$ are not within the predetermined number of beats (e.g., 3 beats) of one another, the one that is in a more physiological range (e.g., as set by a clinician) is identified as, and saved as, the final HR. As mentioned above, the final HR can also be referred to as an estimate of the patient's actual HR. Alternatively, if the $HR_{LAP}$ and the $HR_{IEGM}$ are not within the predetermined number of beats (e.g., 3 beats) of one another, then the final HR can be considered indeterminate.

At step 152 there is a determination of whether the final HR is within the $frange_{VT}$. As mentioned above, an exemplary $frange_{VT}$ is from 181 to 220 bpm. If the answer to the determination at step 152 is yes, then the cardiac rhythm is classified as VT, as shown at step 154. If the answer to the determination at step 152 is no, then at step 156 there is a determination of whether the final HR is within the $frange_{SVT}$. As mentioned above, an exemplary $frange_{SVT}$ is from 121 to 180 bpm. If the answer to the determination at step 156 is no, then at step 160 the cardiac rhythm is classified as SR. Steps 154, 158 and/or 160 can also include saving an indication of the rhythm classification along with a time stamp and/or data corresponding to one or more of the signals and/or frequency power spectrums used for the rhythm classification.

The steps described above with reference to FIGS. 1A and 1B can be continually repeated, repeated from time-to-time (e.g., periodically or aperiodically), performed on demand (e.g., in response to a triggering event), and the like. The final HR, the RR and the cardiac rhythm classification can be saved and displayed to a patient, physician and/or clinician, optionally along with one or more of the waveforms obtained at steps 102 and 122 and/or obtained at steps 104/106 and/or 124/126.

FIGS. 2A, 2B, 2C and 2D illustrate an exemplary atrial IEGM signal, LAP signal, atrial IEGM frequency power spectrum, and LAP frequency power spectrum. In FIG. 2D the maximum peak in the $pDFT_{LAP}$ within the $frange_{RR}$ occurs at 28 breaths per minute, and thus, RR=28 breaths per minute. In FIG. 2C the first peak that exceeds the $thresh_{IEGM}$ is within the $frange_{SR}$ and corresponds to a HR of 96 bpm, resulting in $HR_{IEGM}$=96 bpm. In FIG. 2D the first peak that exceeds the $thresh_{LAP}$ and is above the minimum HR frequency (and is not within a few beats of RR and is not an integer multiple of RR) corresponds to an HR of 96 bpm, resulting in $HR_{LAP}$=96 bpm. Using the embodiments described above with reference to FIGS. 1A and 1B, a sinus rhythm would be detected, and the final HR=$HR_{IEGM}$=96 bpm.

Figures 3A, 3B, 3C, 3D:
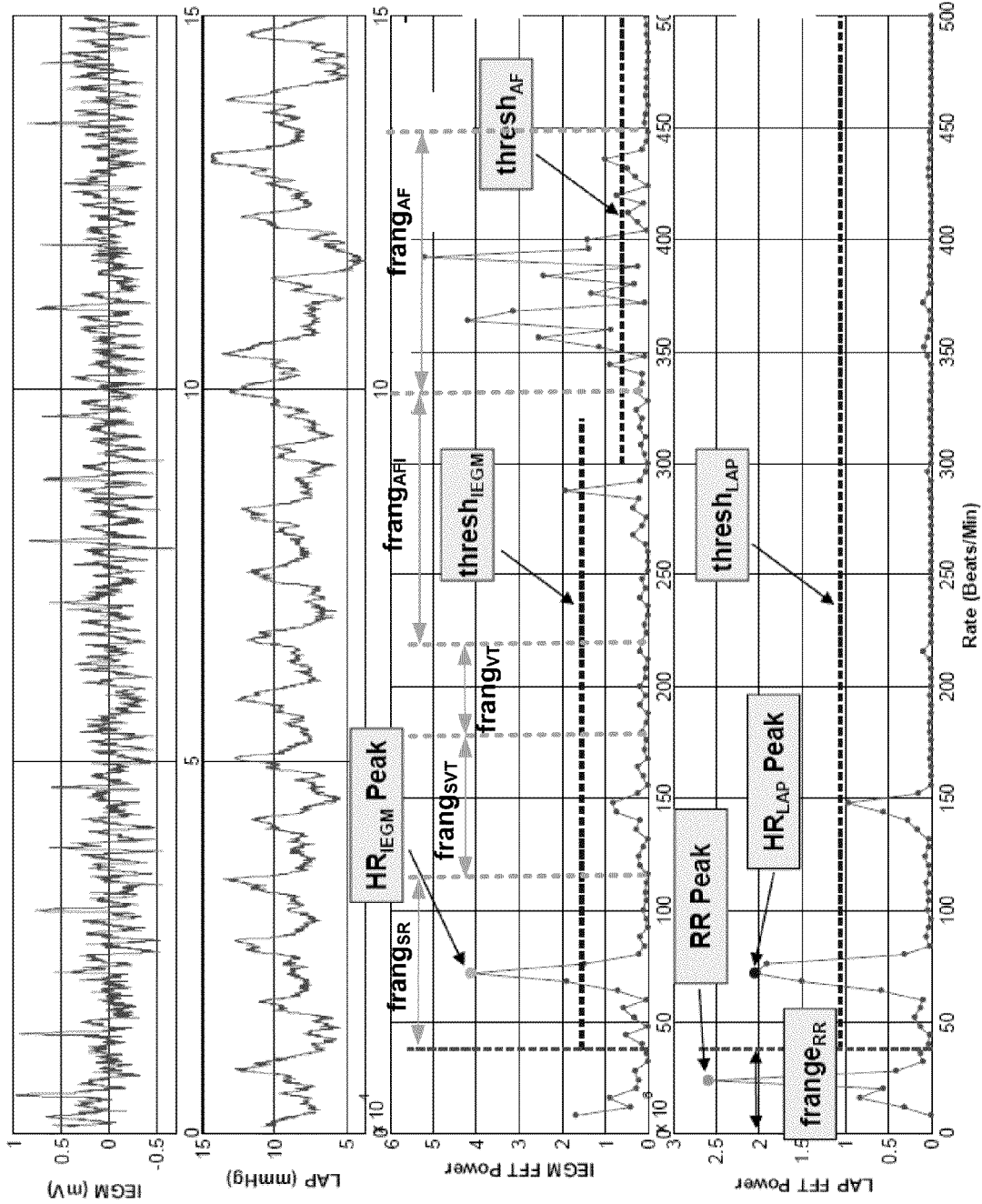
FIGS. 3(a)-3(d) illustrate an exemplary atrial IEGM signal, LAP signal, atrial IEGM frequency power spectrum, and LAP frequency power spectrum, which correspond to a heart rate of 72 beats per minute, a respiration rate of 24 breaths per minute, and which are used to detect atrial fibrillation.

FIGS. 3A, 3B, 3C and 3D illustrate another exemplary atrial IEGM signal, LAP signal, atrial IEGM frequency power spectrum, and LAP frequency power spectrum. In FIG. 3D the maximum peak in the $pDFT_{LAP}$ within the $frange_{RR}$ occurs at 24 breaths per minute, and thus, RR=24 breaths per minute. In FIG. 3C the first peak that exceeds the $thresh_{IEGM}$ is within the $frange_{SR}$ and corresponds to an HR of 72 bpm, resulting in $HR_{IEGM}$=72 bpm. In FIG. 3D the first peak that exceeds the $thresh_{LAP}$ and is above the minimum HR frequency (and is not within a few beats of RR and is not an integer multiple of RR) corresponds to an HR of 72 bpm, resulting in $HR_{LAP}$=72 bpm. Note that in FIG. 3C there are multiple peaks that exceed the $thresh_{IEGM}$ and are within the $frange_{AF}$, which are indicative of AF. Using the embodiments described above with reference to FIGS. 1A and 1B, AF would be detected, and the final HR=$HR_{LAP}$=72 bpm.

FIGS. 4A, 4B, 4C and 4D illustrate a further exemplary atrial IEGM signal, LAP signal, atrial IEGM frequency power spectrum, and LAP frequency power spectrum. In FIG. 4D the maximum peak in the $pDFT_{LAP}$ within the $frange_{RR}$ occurs at 20 breaths per minute, and thus, RR=20 breaths per minute. In FIG. 4C there is no peak that exceeds the $thresh_{IEGM}$ and is within the $frange_{SR}$, and thus, $HR_{IEGM}$ is indeterminate. In FIG. 4D the first peak that exceeds the $thresh_{LAP}$ and is above the minimum HR frequency (and is not within a few beats of RR and is not an integer multiple of RR) corresponds to an HR of 64 bpm, resulting in $HR_{LAP}$=64 bpm. Note that in FIG. 3C there is a peak (at about 227 bpm) in the $pDFT_{IEGM}$ that exceeds the $thresh_{IEGM}$ and is within the $frange_{AFI}$. This peak is indicative of the atrial rate, not the HR (i.e., not the ventricular depolarization rate). Using the embodiments described above with reference to FIGS. 1A and 1B, AFI would be detected, and the final HR=$HR_{LAP}$=64 bpm.

FIGS. 5A, 5B, 5C and 5D illustrate still another exemplary atrial IEGM signal, LAP signal, atrial IEGM frequency power spectrum, and LAP frequency power spectrum. In FIG. 5D the maximum peak in the $pDFT_{LAP}$ within the $frange_{RR}$ occurs at 20 breaths per minute, and thus, RR=20 breaths per minute. In FIG. 5C the first peak that exceeds the $thresh_{IEGM}$ is within the $frange_{SR}$ and corresponds to an HR of 84 bpm, resulting in $HR_{IEGM}$=84 bpm. In FIG. 5D the first peak that exceeds the $thresh_{LAP}$ and is above the minimum HR frequency (and is not within a few beats of RR and is not an integer multiple of RR) corresponds to an HR of 84 bpm, resulting in $HR_{LAP}$=84 bpm. Using the embodiments described above with reference to FIGS. 1A and 1B, a sinus rhythm would be detected, and the final HR=$HR_{IEGM}$=84 bpm.

Embodiments of the present invention described above can be used to monitor and treat cardiovascular disease, and more specifically, can be used to determine heart rate (HR), determine respiration rate (RR) and classify cardiac rhythms based on atrial intracardiac electrogram (IEGM) and left atrial pressure (LAP) signals. Based on the HR, RR and/or rhythm classification, a patient can be instructed to take specific medications and/or to call or visit a physician. Exemplary devices and systems that can be used to implement such embodiments are describe below with reference to FIGS. 6-10.

Figure 6:
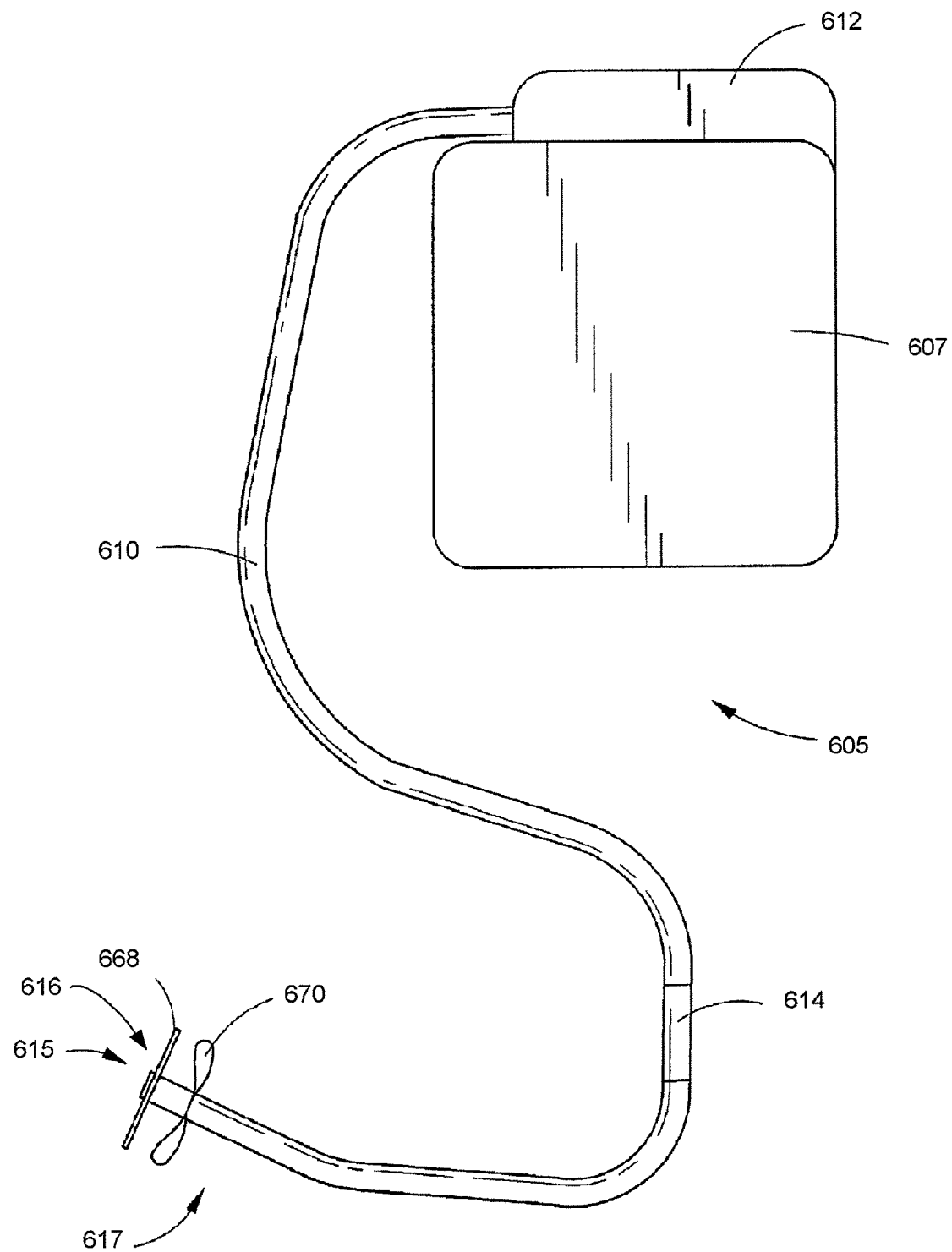
FIG. 6 depicts an implantable apparatus suitable for practicing various embodiments of the invention.

FIG. 6 shows an apparatus for monitoring and potentially treating cardiovascular disease, such as CHF, which includes an implantable module 605 in accordance with one embodiment of the invention. The implantable module 605 (which can also be referred to as an implantable system) includes a housing 607 and a flexible lead 610. The module 605 can be, e.g., a physiologically optimized dosimeter (POD™), such as the HEARTPOD™ device developed by the St. Jude Medical of St. Paul, Minn. Cardiovascular disease, as used herein, shall be given its ordinary meaning, and shall also include high blood pressure, diabetes, coronary artery disease, valvular heart disease, congenital heart disease, arrhythmia, cardiomyopathy, and CHF.

The lead 610 is connectable to the housing 607 through a connector 612 (also known as a header) that may be located on the exterior of the housing. In one embodiment, the housing 607 is outwardly similar to the housing of an implantable electronic defibrillator and/or pacemaker system. Defibrillator and pacemaker systems are implanted routinely in medical patients for the detection and control of tachy- and bradyarrhythmias. The flexible lead 610 is also generally similar to leads used in defibrillator and pacemaker systems, except that a compact sensor package 615 is disposed at or near the distal end 617 of the lead 610, the opposite end from the connector 612 on the housing 607. The sensor package 615 includes a left atrial pressure (LAP) sensor, and optionally one or more further sensors to measure one or more further physical parameters. Signals from the pressure sensor are monitored continuously or at appropriate intervals. Information is then communicated to the patient corresponding to appropriate physician-prescribed drug therapies. In one embodiment, the information is the treatment signal. In many cases, the patient may administer the drug therapies to him or herself without further diagnostic intervention from a physician.

The lead 610 includes an indifferent electrode 614 which is implanted in the right atrium. The lead 610 can also include a left atrial electrode 616 (e.g., a left atrial ring or tip electrode) in close proximity to the sensor package 615. Signals indicative of LAP (as detection using the LAP sensor 615) and sensed cardiac electrical activity (e.g., as detected using electrode 614 and/or 616) is transmitted along the lead 610 through the connector 612 and to electronic circuitry within the housing 607.

The housing 607 includes a signal processor (e.g., 757 in FIG. 7) to process the signal received from the sensor package 615 via the lead 610. The signal processor can also process the atrial IEGM obtained using electrode(s) of the lead 610. In addition, the housing 607 may include a telemetry and/or patient signaling module (e.g., 759 in FIG. 7), to either communicate with an external device, or signal the patient, or both. The elements inside the housing 607 may be configured in various ways, as described below, to communicate to the patient a signal, such as a treatment signal, indicative of an appropriate therapy or treatment based at least in part on one or more of the measured physical parameters.

FIG. 6 also shows that the sensor package or module 615 has distal 668 and proximal 670 anchoring mechanisms configured to anchor the sensor package 615 within the atrial septum of a patient's heart. One embodiment showing the contents of the housing 607 is illustrated in FIG. 7.

The housing 607 can have a shape that is flat and oval. In another embodiment, the shape is cylindrical, rectangular, elliptical, or spherical. One of skill in the art will understand that a variety of other shapes suitable for implantation can also be used. In one embodiment, the housing is about 20 mm by about 30 mm, about 10 mm by about 20 mm, or about 5 mm by about 10 mm. In one embodiment, the housing is about 5 mm thick. In one embodiment, the housing is implanted in the patient near the shoulder. In another embodiment, the housing has dimensions suitable for containing at least some components for controlling, powering and/or communicating with a pacemaker and suitable for implantation inside of the body, as is well known to those of skill in the art. In another embodiment, the housing includes: an antenna, or a coil; a power source, including but not limited to a battery or a capacitor; a signal processor; a telemetry apparatus; a data memory; or a signaling device. In one embodiment, the apparatus is powered by an external power source through inductive, acoustical, or radio frequency coupling. In one embodiment, power is provided using electromagnetic emissions emitted from an electrical coil located outside the body. In one embodiment, power and data telemetry are provided by the same energy signal. In another embodiment, an electrical coil is implanted inside the body at a location under the skin near the patient's collarbone. In another embodiment, an electrical coil is implanted inside the patient's body at other locations. For example, in one embodiment, the coil is implanted under the skin in the lower abdomen, near the groin. One of skill in the art will understand that the device can be implanted in a variety of other suitable locations.

Figure 7:
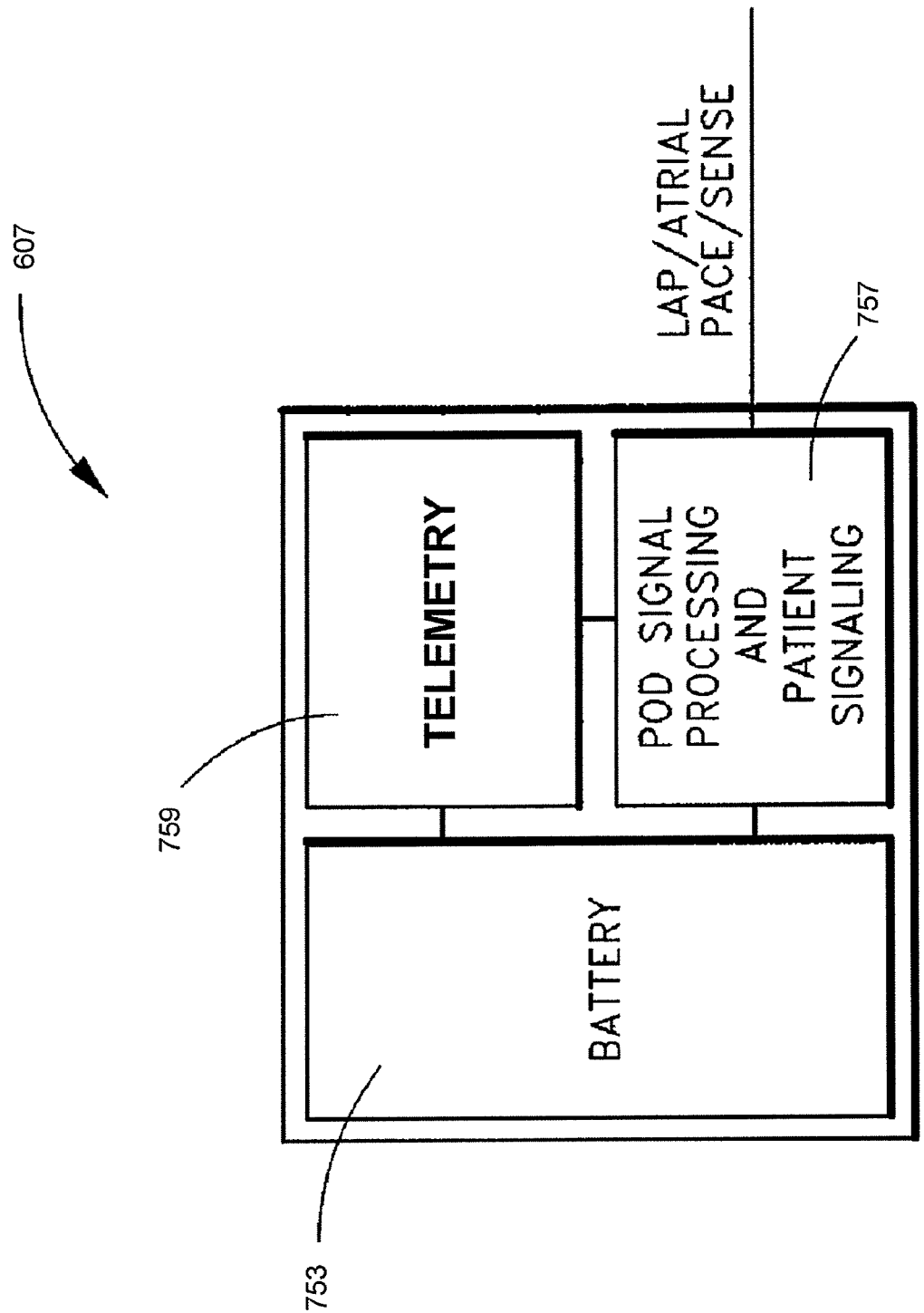
FIG. 7 is a schematic of one embodiment of the electronics located within the implantable housing of the implantable apparatus illustrated in FIG. 6.

As shown in FIG. 7, in one embodiment housing 607 includes a battery 753, signal processing and patient signaling modules 757, and a telemetry module 759 with an associated antenna (not shown), which is coupled to the module 757. The housing 607 can optionally also include a cardiac rhythm management (CRM) system, which is configured to provide an electrical stimulus, such as a pacing signal and/or a defibrillation shock, to the patient's heart. The signal processing module 757 is coupled to at least one LAP sensor that provides a signal indicative of the fluid pressure within the left atrium of the heart. The signal processing module 757 is also coupled to the one or more electrodes of the lead 610, as well as to the electrically conductive "can", thereby enabling the module 757 to obtain an atrial IEGM signal. In accordance with an embodiment, the signal processing module 757 can perform the various steps described above with reference to FIGS. 1A and 1B. The signal processing module 757 may also be configured to control distally implanted CRM components, or a sensor package or module, as described in greater detail herein. The signal processing module 757 can include memory and/or registers for storing signals and/or values obtained using embodiments of the present invention described above.

Figure 8:
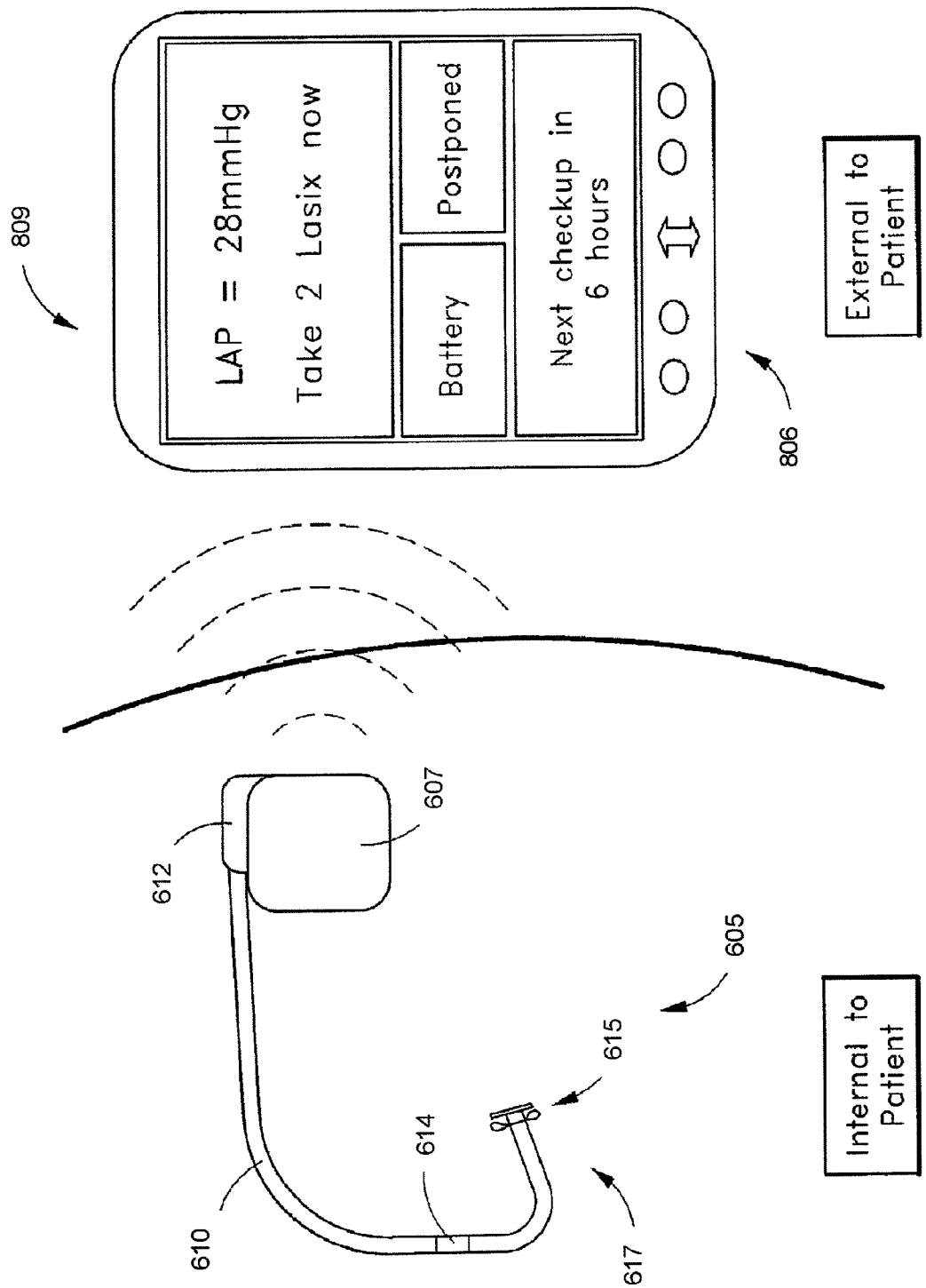
FIG. 8 is a system for treating cardiovascular disease according to an embodiment of the present invention.

FIG. 8 shows one embodiment of a system 809 for monitoring and potentially treating cardiovascular disease. The system 809 includes the implantable module 605, which was described with reference to FIG. 6, and an external PAM 806, such as that described below with reference to FIG. 9. During system operation, radio frequency (RF) or other types of signals are carried by the lead 610 between the LAP sensor package 615 located near the distal end 617 of the lead 610, and the housing 607 of the implantable module 605. The circuitry inside the housing 607 includes an antenna coil (not shown). In this embodiment, signals are communicated between the implantable module 605 and an external device, such as a patient advisory module (PAM) 806, via the antenna coil of the housing 607 and a second external coil (not shown) coupled to the external device 806.

As was shown in FIG. 7, the housing 607 contains a battery 753 that powers the implantable device 605. In another embodiment, the implanted device 605 receives power and programming instructions from an external device 806 via radio frequency (RF) transmission between the external and internal coils. The external device 806 receives signals indicative of one or more physiological parameters from the implanted device 605 via the coils as well. One advantage of such externally powered implantable device 605 is that the patient will not require subsequent surgery to replace a battery. In one embodiment of the present invention, power is required only when the patient or the patient's caregiver initiates a reading. In other situations, where it is desired to obtain physiological information continuously, or where it is desired that the implanted device 605 also perform functions with higher or more continuous power requirements, it is preferable that the housing 607 contain one or more batteries. As described below, the housing 607 may also contain circuitry to perform additional functions that may be desirable.

Figure 9:
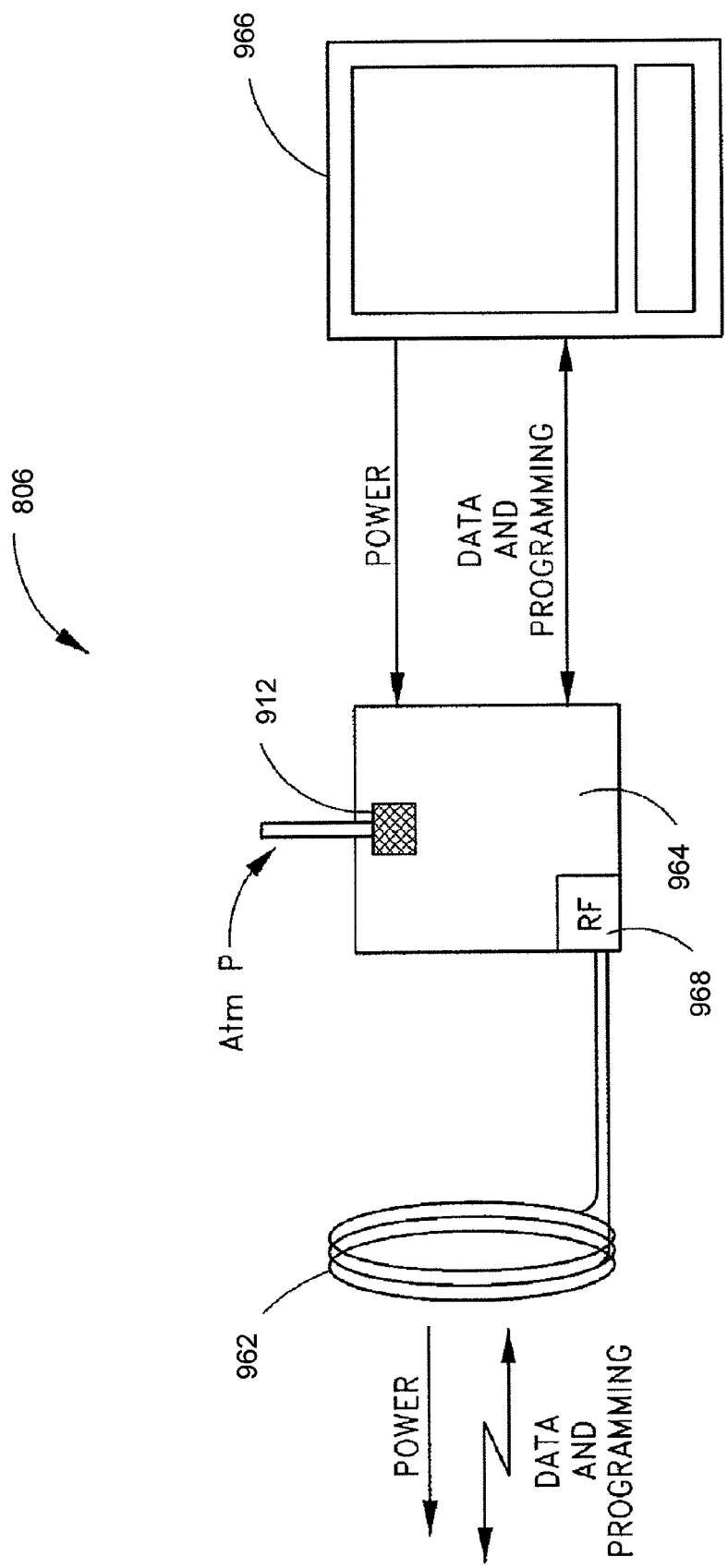
FIG. 9 is a block diagram of an external patient advisor/telemetry module for use in an embodiment of the present invention.

FIG. 9 shows one embodiment of the PAM 806. In one embodiment, the PAM 806 includes a hand held computer with added hardware and software. Referring to FIG. 9, a PAM 806 includes a radio frequency telemetry module 964 with an associated coil antenna 962, which is coupled to a processing unit 966. In one embodiment, the processing unit 966 includes a palm-type computer, or personal digital assistant (PDA), or a tablet computer, as is well known to those of skill in the art. In one embodiment, the PAM 806 powers the implanted module (605 in FIGS. 6 and 8) with the telemetry hardware module 964 and coil antenna 962. In another embodiment, the PAM 806 receives physiological signals from the implanted module by wireless telemetry through the patient's skin.

The PAM 806 may include an RF unit 968 and a barometer 912 for measuring the reference atmospheric pressure. In one embodiment, the RF unit 968 and barometer are located within the telemetry module 964, although they can be integrated with the processing unit 966 as well. The signal processing unit can be used to analyze physiologic signals and to determine physiologic parameters. The PAM 966 may also include data storage, and a sub-module that contains the physician's instructions to the patient for therapy and how to alter therapy based on changes in physiologic parameters. The parameter based physician's instructions are typically referred to as "the dynamic prescription," or DynamicRx™ (St. Jude Medical Inc.). The instructions are communicated to the patient via the signaling module 966, or another module. The PAM 966 is located externally and used by the patient or his direct caregiver. It may be part of a system integrated with a personal digital assistant, a cell phone, or a personal computer, or as a Stand-Alone device. In one embodiment, the external PAM comprises an external telemetry device, a signal processing apparatus, and a patient signaling device. In one embodiment, the PAM is operated to obtain the sensor signal from the implantable sensor by telemetry through the patient's skin; obtain the atmospheric pressure from the barometer; and adjust the sensor signal indicative of a fluid pressure based at least in part upon the atmospheric pressure obtained by the barometer so that the adjusted sensor signal indicates the fluid pressure within the left atrium of the heart relative to the atmospheric pressure.

In one embodiment, the physiologic signals are analyzed and used to determine adjustable prescriptive treatment instructions that have been placed in the PAM 806 by the patient's personal physician. Communication of the prescriptive treatment instructions to the patient may appear as written or graphic instructions on a display of the PAM 806. These treatment instructions may include what medications to take, dosage of each medication, and reminders to take the medications at the appropriate times. In one embodiment, the PAM 806 displays other physician-specified instructions, such as "Call M.D." or "Call 911" if monitored values become critical.

A third module of this embodiment is designed for physician use. The third module is used to program the dynamic prescription and communicate it or load it into the PAM 806. The third module may also contain stored data about the patient, including historical records of the physiologic signals and derived parameters transmitted from the patient implant and signaling modules. The third module may also communicate with external databases. In one embodiment, the third module is a physician input device, and includes a personal computer, a mobile phone, a table computer, a PDA, or any other such device as is well known to those of skill in the art.

In one embodiment of the present invention, the first implant module (such as, for example, implantable module 605 of FIG. 6) may also contain an implant therapy unit, or ITU. The ITU generates an automatic therapy regimen based upon the programmed dynamic prescription. The therapy may include, but is not limited to, a system for releasing bioactive substances from an implanted reservoir, a system for controlling electrical pacing of the heart, and controllers for ventricular or other types of cardiac assist devices. For example, in one embodiment the sensor package is placed across the intra-atrial septum and serves as the atrial lead of a multichamber pacemaker. The physiologic sensor information is used to adjust pacing therapy such that pacing is performed only when needed to prevent worsening heart failure. One skilled in the art will appreciate that many systems or devices that control the function of the cardiovascular system may be used in accordance with several embodiments of the current invention.

In one embodiment of the invention, the advisory module 806 is programmed to signal the patient when it is time to perform the next cardiac status measurement and to take the next dose of medication. It will be recognized by those skilled in managing CHF patients that these signals may help the many patients who have difficulty taking their medication on schedule. Although treatment prescriptions may be complex, one embodiment of the current invention simplifies them from the patient's perspective by providing clear instructions. To assure that information regarding the best treatment is available to physicians, professional cardiology organizations such as the American Heart Association and the American College of Cardiology periodically publish updated guidelines for CHF therapy. These recommendations can serve as templates for the treating physician to modify individual patient treatment. In one embodiment, the device routinely uploads data to the physician or clinic, so that the efficacy of the prescription and the response to parameter driven changes in dose can be monitored. This enables the physician to optimize the patient's medication dosage and other important treatments without the physician's moment-to-moment intervention.

In various embodiments of the invention, a device and method for dynamically diagnosing and treating cardiovascular illness in a patient are provided. In one embodiment, at least one physiological sensor is used to generate a signal indicative of a physiological parameter. In another embodiment, signal processing apparatus operable to generate a signal indicative of an appropriate therapeutic treatment based, at least in part, upon the signal generated by the physiological sensor, is also provided. In another embodiment a patient signaling device used to communicate the signal indicative of the appropriate therapeutic treatment to the patient is provided as well.

In one embodiment, a device and method for continuously or routinely monitoring the condition of a patient suffering from chronic cardiovascular disease are provided. As will be described in detail below, a system incorporating various embodiments of the invention monitors various physiologic parameters, such as the patient's left atrial pressure. Depending upon the magnitude of or changes in this pressure, for example, the system communicates a signal to the patient indicative of a particular course of therapy appropriate to manage or correct, as much as possible, the patient's chronic condition. In some embodiments, physician instructions and automated therapy are provided.

In one embodiment, the physiological sensor generates a signal indicative of a physiological parameter on or in the patient's body. In one embodiment, the signal processing apparatus generates a signal indicative of an appropriate therapeutic treatment based at least in part upon the signal generated by the physiological sensor. The patient signaling device may generate signals indicative of therapeutic treatments or courses of action the patient can take to manage or correct, as much as possible, the patient's condition.

In one embodiment, this method includes the steps of implanting one or more physiological sensors substantially permanently within the patient, operating the physiological sensor to generate a signal indicative of a physiological parameter, processing this physiological signal to generate a signal indicative of an appropriate therapeutic treatment, and communicating the appropriate therapeutic treatment to a user. In one embodiment, the user includes, but is not limited to, the patient, a caregiver, a medical practitioner or a data collection center.

In another embodiment, the system is combined with or incorporated into a CRM system, with or without physiologic rate control, and with or without backup cardioversion/defibrillation therapy capabilities.

In one embodiment, at least one indication of congestive heart failure (CHF) is monitored. Elevated pressure within the left atrium of the heart is the precursor of fluid accumulation in the lungs, which results in signs and symptoms of acute CHF. Mean left atrial pressure in healthy individuals is normally less than or equal to twelve millimeters of mercury (mm Hg). Patients with CHF that have been medically treated and clinically "well compensated" may generally have mean left atrial pressures in the range from 12 to 20 mm Hg. Drainage of fluid into the pulmonary interstitial spaces can be expected to occur when the left atrial pressure is above about twenty-five mm Hg, or at somewhat more than about thirty mm Hg in some patients with chronic CHF. Pulmonary edema has been found to be very reliably predicted by reference to left atrial pressures and less well correlated with conditions in any other chamber of the heart. Thus, the methods and apparatus of several embodiments of the invention may prove very useful in treating and preventing pulmonary edema and other adverse conditions associated with CHF. Pressure in the pulmonary veins, pulmonary capillary wedge position, and left ventricular end diastolic pressure (LVEDP) are generally indicative of left atrial pressure and are commonly used as surrogates of LAP. There are, however, specific conditions, that are well known to those skilled in the art, including cardiologists and physiologists, where these surrogates vary substantially from LAP and may be less predictive of impending heart failure. One example of such a condition is mitral valve stenosis where pulmonary edema develops despite a normal LVEDP due to a significant pressure gradient across the mitral valve. Other surrogate pressures that also, on specific occasion, indicate LAP include, but are not limited to: the pulmonary artery diastolic (PAD) or algorithms that estimate PAD from the right ventricular waveform, the right ventricular end diastolic, and the right atrial pressure.

An embodiment of the invention includes a permanently implanted device designed to define the presence of worsening CHF hours to days before the onset of symptoms and to provide for early preventative treatment according to the physician's individualized prescription. As such, an embodiment of the invention includes an integrated patient therapeutic system that determines therapeutic dosages for an individual patient based at least in part on internal physiologic signals. In another embodiment, the system consists of a small implantable sensor device and an external PAM comprising a personal data assistant (PDA) and a telemetry module. The sensor system may be implanted into the patient's left atrial chamber by a transseptal catheterization procedure. There are already several thousand physicians in the U.S. and abroad with the experience and skills required for such device implantation. The implantation procedure can be performed on an outpatient basis in a hospital's cardiac catheterization laboratory. The implant may alternatively be placed at the time of open-heart or minimally invasive valve or bypass surgery where the surgeon, under direct or laparoscopic vision, positions the device in the left atrium, left atrial appendage, or an adjacent pulmonary vein.

In one embodiment, the sensor system obtains LAP and atrial IEGM signals. Elevated left atrial pressure is the most accurate predictor of impending CHF, often preceding clinical symptoms by hours to days. Other embodiments of the left atrial pressure waveform may be used to diagnose a number of conditions. The sensor package 615 may also include a temperature sensor to monitor core temperature, which is often depressed in acute CHF, but elevated prior to the development of fever in response to an infection, making core temperature a useful parameter for differentiating between these common conditions with similar symptoms which require different treatments. The atrial IEGM may be useful in diagnosing arrhythmias and precipitating causes of worsening CHF.

Figure 10:
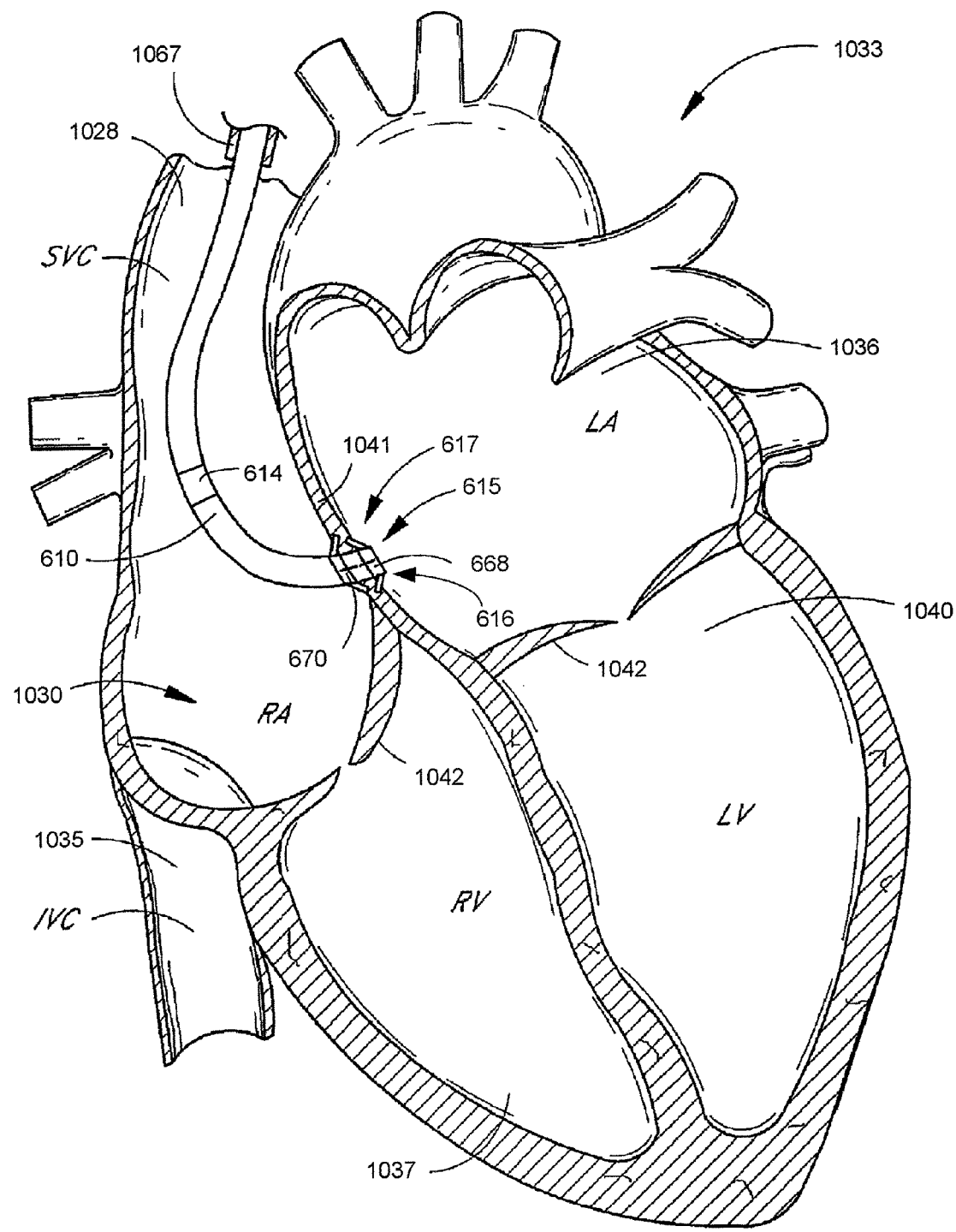
FIG. 10 shows a flexible lead having an LAP sensor in fluid contact with the patient's left atrium.

In one embodiment, such as that illustrated in FIG. 10, an implantable device is implanted percutaneously in the patient by approaching the left atrium 1036 through the right atrium 1030, penetrating the patient's atrial septum 1041 and positioning the sensor package 615 in the atrial septum 1041, on the septal wall of the left atrium 1036, or inside the patient's left atrium 1036. FIG. 10 shows an embodiment in which the sensor package 615 is deployed across the atrial septum 1041. The sensor lead 610 is coupled to a physiological sensor or sensors 615 and anchoring apparatus at the lead 610 distal end 617. The anchoring apparatus includes a distal foldable spring anchor 668 that expands in diameter upon release and is located at or near the distal tip of the sensor 615, and a proximal foldable spring anchor 670. The distal and proximal anchors 668, 670 are sufficiently close together that when deployed the two anchors 668, 670 sandwich the intra-atrial septum 1041 between them, thus fixing the sensor/lead system to the septal wall. The intra-atrial septum 1041 is typically between about 1 and about 10 mm thick. In one embodiment, the anchors 668, 670 are made of a highly elastic biocompatible metal alloy such as superelastic nitinol. The lead 610 may contain a lumen that exits the lead 610 at its proximal end.

In accordance with an embodiment, a stiffening or bending stylet can be insert in the lumen to aid in passage of the sensor(s) 615 and lead 610. After a transseptal catheterization has been performed, a sheath/dilator system of diameter sufficient to allow passage of the sensor/lead system is placed from a percutaneous insertion site over a guidewire until the distal end of a sheath 1067 is in the left atrium 1036. Left atrial position can be confirmed under fluoroscopy by contrast injection, or by the pressure waveform obtained when the sheath 1067 is connected to a pressure transducer. To aid the procedure, the sheath 1067 may include a proximal hemostasis valve to minimize air entrainment during device insertion. A side port with a stopcock is useful to aspirate any remaining air and to inject radiographic contrast material. Additionally, later sheath 1067 removal may be facilitated by using a "peel-away" type of sheath. These features of vascular sheaths are commercially available and well know to those familiar with the art. With the spring anchors 668, 670 folded and forming a system with minimal diameter, the system is loaded into the sheath 1067 and advanced until the distal spring 668 just exits the sheath 1067 in the left atrium 1036 and is thus deployed to its sprung diameter. The sheath 1067 is carefully withdrawn without deploying the proximal anchor 670 and the sheath 1067 and sensor/lead system are withdrawn as a unit while contrast is injected through the sheath 1067 around the sensor lead until contrast is visible in the right atrium 1030. The proximal sheath 1067 is further withdrawn, allowing the proximal anchor 670 to spring to its unloaded larger diameter, thus fixing the distal portion of the sensor lead to the septum 1041.

It will also be apparent that, in several embodiments, a similar sensor/lead system can be inserted through an open thoracotomy or a minimally invasive thoracotomy, with the anchoring system fixating the sensor/lead to a location such as the free wall of the left atrium, the left atrial appendage, or a pulmonary vein, all of which provide access to pressures indicative of left atrial pressure.

Embodiments of the present invention have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 1A and 1B. For another example, it is possible to change the boundaries of some of the blocks shown in FIG. 7.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

The invention claimed is:

1. A system, comprising:
    an implantable device including an electrically conductive housing;
    one or more implantable leads attachable to the implantable device and individually or collectively including an implantable pressure sensor and one or more electrodes;
    circuitry configured to obtain, using at least one of the one or more electrodes, and optionally the electrically conductive housing, an atrial intracardiac electrogram (IEGM) signal;
    circuitry configured to obtain, using the pressure sensor, an atrial pressure (AP) signal indicative of pressure in an atrium;
    one or more processor configured to
        subject the atrial IEGM signal to a spectrum transform to obtain an atrial IEGM frequency spectrum;
        subject the AP signal to a spectrum transform to obtain an AP frequency spectrum;
        determine a first measure of heart rate ($HR_{IEGM}$) based on one or more peaks in the atrial IEGM frequency spectrum; and
        determine a second measure of heart rate ($HR_{AP}$) and a measure of respiratory rate ($RR_{AP}$) based on one or more peaks in the AP frequency spectrum.

2. The system of claim 1, wherein the first measure of heart rate ($HR_{IEGM}$) can be indeterminate, and wherein the one or more processor is configured to:
    determine an estimate of the patient's actual heart rate based on at least one of the first and second measures of heart rate; and
    wherein the estimate of the patient's actual heart rate is saved, uploaded and/or displayed along with the measure of respiratory rate ($RR_{AP}$).

3. The system of claim 1, wherein the one or more processor is configured to:
    identify one or more peaks, if any, in the atrial IEGM frequency spectrum that exceed an IEGM threshold ($thresh_{IEGM}$) and is/are within a sinus rhythm frequency range ($frange_{SR}$); and
    determine the first measure of heart rate ($HR_{IEGM}$) based on the one or more identified peaks in the atrial IEGM frequency spectrum that exceed the $thresh_{IEGM}$ and is/are within the $frange_{SR}$.

4. The system of claim 1, wherein the one or more processor is configured to:
    identify one or more peaks in the AP frequency spectrum that is/are within a respiratory rate frequency range ($frange_{RR}$); and
    determining the measure of respiratory rate ($RR_{AP}$) based on the one or more identified peaks within the $frange_{RR}$.

5. The system of claim 4, wherein the one or more processor is configured to:
    identify one or more peaks in the AP frequency spectrum that exceeds an AP threshold ($thresh_{AP}$) and is/are above a minimum heart rate or within a heart rate frequency range ($frange_{HR}$); and
    determine the second measure of heart rate ($HR_{AP}$) based on the one or more identified peaks in the AP frequency spectrum that exceed the $thresh_{AP}$ and is/are above the minimum heart rate or within the $frange_{HR}$.

6. The system of claim 1, wherein the one or more processor is configured to:
    detect arrhythmias and/or perform arrhythmia discrimination based on one or more peaks in the atrial IEGM frequency spectrum and one or more peaks in the AP frequency spectrum.

7. The system of claim 1, wherein the one or more implantable leads comprise a single lead including the implantable pressure sensor and the one or more electrodes.

* * * * *